United States Patent
Mizutani et al.

(10) Patent No.: US 6,994,780 B2
(45) Date of Patent: *Feb. 7, 2006

(54) GAS SENSOR AND METHOD OF DETECTING GAS CONCENTRATION

(75) Inventors: Keigo Mizutani, Okazaki (JP); Kazunori Suzuki, Nagoya (JP); Toshitaka Saito, Toyohashi (JP); Daisuke Makino, Ichinomiya (JP)

(73) Assignees: Denso Corporation, (JP); Nippon Soken, Inc., (JP)

( * ) Notice: Subject to any disclaimer, the term of this patent is extended or adjusted under 35 U.S.C. 154(b) by 478 days.

This patent is subject to a terminal disclaimer.

(21) Appl. No.: 10/234,248

(22) Filed: Sep. 5, 2002

(65) Prior Publication Data

US 2003/0042152 A1  Mar. 6, 2003

(30) Foreign Application Priority Data

Sep. 5, 2001 (JP) ............................. 2001-269383
Jul. 29, 2002 (JP) ............................. 2002-220046

(51) Int. Cl.
  *G01N 27/407* (2006.01)

(52) U.S. Cl. .................. 205/787; 205/784.5; 204/425; 204/427

(58) Field of Classification Search ................ 204/421, 204/424–428; 205/782–786, 787; 73/23.31
See application file for complete search history.

(56) References Cited

U.S. PATENT DOCUMENTS 4,306,957 A * 12/1981 Ishitani et al. .............. 204/412
5,985,118 A    11/1999 Makino et al.
6,214,207 B1 *  4/2001 Miyata et al. .............. 205/781
6,495,027 B1 * 12/2002 Stahl et al. ................. 205/781
6,740,217 B2 *  5/2004 Mizutani et al. ............ 204/426

FOREIGN PATENT DOCUMENTS

| EP | 0 678 740 A1 | 10/1995 |
| JP | 8-271476 | 10/1996 |
| JP | 10-132782 | 5/1998 |
| JP | 10-185868 | 7/1998 |
| WO | WO 102845 A1 * | 1/2001 |

* cited by examiner

Primary Examiner—Kaj Olsen
Assistant Examiner—R. Michelle Vestal
(74) Attorney, Agent, or Firm—Nixon & Vanderhye PC

(57) ABSTRACT

A gas sensor includes a measurement gas chamber into which a measurement gas is introduced. An oxygen pumping cell adjusts an oxygen concentration in the measurement gas chamber. An oxygen monitor cell has a monitor electrode exposed in the measurement gas chamber. The monitor electrode has an oxidizing activity with respect to a specific component of the measurement gas. A sensor cell has a sensor electrode exposed in the measurement gas chamber. The sensor electrode has an oxidizing activity with respect to the specific component of the measurement gas which is lower than the oxidizing activity of the monitor electrode. An oxygen-ion current in the oxygen monitor cell is detected. An oxygen-ion current in the sensor cell is detected. A concentration of the specific component of the measurement gas is detected from a relation between the detected oxygen-ion currents in the oxygen monitor cell and the sensor cell.

23 Claims, 10 Drawing Sheets

GAS SENSOR AND METHOD OF DETECTING GAS CONCENTRATION

BACKGROUND OF THE INVENTION

1. Field of the Invention

This invention relates to a gas sensor for detecting a specific-component concentration in a gas. In addition, this invention relates to a method of detecting a specific-component concentration in a gas.

2. Description of the Related Art

European patent application publication number 0678740 A1 corresponding to Japanese patent application publication number 8-271476 discloses a sensing device for measuring a concentration of a gas component of a measurement gas. The sensing device in European application 0678740 A1 includes a first internal space into which the measurement gas is introduced from an external measurement-gas space via a first diffusion controlling passage. A flow of the measurement gas toward the first internal space receives a predetermined diffusion resistance provided by the first diffusion controlling passage. The first internal space communicates with a second internal space via a second diffusion controlling passage. The atmosphere is introduced from the first internal space into the second internal space via the second diffusion controlling passage under a predetermined diffusion resistance provided by the second diffusion controlling passage. A first oxygen pumping means operates to control an oxygen partial pressure in the first internal space. A second oxygen pumping means operates to pump out oxygen from the atmosphere in the second internal space toward a reference-gas channel. An ammeter detects a pumping current caused by the pumping action of the second oxygen pumping means. The concentration of the gas component of the measurement gas is measured from the detected pumping current.

U.S. Pat. No. 5,985,118 corresponding to Japanese patent application publication number 10-185868 discloses a gas concentration detector using solid electrolyte layers laminated. The gas concentration detector measures a concentration of gas constituents in measuring gas such as exhaust gas of an internal combustion engine without being influenced by oxygen concentration in the measuring gas. The measuring gas is introduced into an inner cavity of the detector, and outside air as a reference gas is introduced into an air passage in the detector. Oxygen concentration in the measuring gas in the inner cavity is maintained at a predetermined level by operation of an oxygen pumping cell constituted by an ion conductive solid electrolyte layer and a pair of electrodes formed on both surfaces of the layer. The oxygen concentration in the inner cavity is measured by an oxygen sensor cell having one electrode exposed to the measuring gas in the inner cavity and the other electrode exposed to the reference gas. The concentration of the gas constituents in the measuring gas is measured in terms of ion current generated in a detector cell constituted by an ion conductive solid electrolyte layer and a pair of electrodes formed on both surfaces of the layer, one electrode being exposed to the measuring gas in the inner cavity and the other exposed to the reference gas in the air passage. Either one of the sensor cell and detector cell electrodes exposed to the measuring gas in the inner cavity is made of a material active to the gas constituents to be measured and the other electrode is made of a material inactive thereto.

As will be explained later, a prior-art hydrocarbon gas sensor tends to have an error in the result of detection of a hydrocarbon gas concentration in the case where measurement environments vary.

SUMMARY OF THE INVENTION

It is a first object of this invention to provide a gas sensor for detecting a specific-component concentration in a gas which is accurate even when measurement environments vary.

It is a second object of this invention to provide a method of detecting a specific-component concentration in a gas which is accurate even when measurement environments vary.

A first aspect of this invention provides a gas sensor comprising a measurement gas chamber; first means for introducing a measurement gas into the measurement gas chamber under a prescribed diffusion resistance; an oxygen pumping cell for adjusting an oxygen concentration in the measurement gas chamber, the oxygen pumping cell having 1) a first solid electrolyte member, 2) a first pumping electrode, and 3) a second pumping electrode, the first solid electrolyte member having an oxygen-ion conductivity, the first pumping electrode being exposed in the measurement gas chamber and extending on a first surface of the first solid electrolyte member, the second pumping electrode extending on a second surface of the first solid electrolyte member and being separate from the measurement gas chamber; second means for applying a voltage between the first and second pumping electrodes to activate the oxygen pumping cell; an oxygen monitor cell having 1) a second solid electrolyte member, 2) a first monitor electrode, and 3) a second monitor electrode, the second solid electrolyte member having an oxygen-ion conductivity, the first monitor electrode being exposed in the measurement gas chamber and extending on a first surface of the second solid electrolyte member, the first monitor electrode having an oxidizing activity with respect to a specific component of the measurement gas, the second monitor electrode being exposed to a reference gas and extending on a second surface of the second solid electrolyte member; a sensor cell having 1) a third solid electrolyte member, 2) a first sensor electrode, and 3) a second sensor electrode, the third solid electrolyte member having an oxygen-ion conductivity, the first sensor electrode being exposed in the measurement gas chamber and extending on a first surface of the third solid electrolyte member, the first sensor electrode having an oxidizing activity with respect to the specific component of the measurement gas which is lower than the oxidizing activity of the first monitor electrode, the second sensor electrode being exposed to the reference gas and extending on a second surface of the third solid electrolyte member; third means for applying a voltage between the first and second monitor electrodes; fourth means for detecting an oxygen-ion current in the oxygen monitor cell when the third means applies the voltage between the first and second monitor electrodes; fifth means for applying a voltage between the first and second sensor electrodes; sixth means for detecting an oxygen-ion current in the sensor cell when the fifth means applies the voltage between the first and second sensor electrodes; and seventh means for detecting a concentration of the specific component of the measurement gas from a relation between the oxygen-ion currents detected by the fourth and sixth means.

A second aspect of this invention provides a method of detecting a gas concentration which is implemented in a gas sensor comprising a measurement gas chamber, an oxygen pumping cell having a pumping electrode exposed in the measurement gas chamber, an oxygen monitor cell having a monitor electrode which is exposed in the measurement gas chamber and has an oxidizing activity with respect to a specific component of a measurement gas, and a sensor cell having a sensor electrode which is exposed in the measurement gas chamber and has an oxidizing activity with respect to the specific component of the measurement gas, wherein the oxidizing activity of the sensor electrode is lower than that of the monitor electrode. The method comprises the steps of introducing the measurement gas into the measurement gas chamber under a prescribed diffusion resistance; applying a voltage to the oxygen monitor cell; applying a voltage to the sensor cell; detecting an oxygen-ion current in the oxygen monitor cell; detecting an oxygen concentration in the measurement gas chamber from the detected oxygen-ion current in the oxygen monitor cell; applying a voltage to the oxygen pumping cell; controlling the voltage applied to the oxygen pumping cell in response to the detected oxygen concentration in the measurement gas chamber to adjust the oxygen concentration in the measurement gas chamber; detecting an oxygen-ion current in the sensor cell; and detecting a concentration of the specific component of the measurement gas from a relation between the detected oxygen-ion current in the oxygen monitor cell and the detected oxygen-ion current in the sensor cell.

A third aspect of this invention provides a gas sensor comprising a measurement gas chamber; first means for introducing a measurement gas into the measurement gas chamber under a prescribed diffusion resistance; an oxygen pumping cell for adjusting an oxygen concentration in the measurement gas chamber, the oxygen pumping cell having 1) a first solid electrolyte member, 2) a first pumping electrode, and 3) a second pumping electrode, the first solid electrolyte member having an oxygen-ion conductivity, the first pumping electrode being exposed in the measurement gas chamber and extending on a first surface of the first solid electrolyte member, the first pumping electrode having an oxidizing activity with respect to a specific component of the measurement gas, the second pumping electrode extending on a second surface of the first solid electrolyte member and being separate from the measurement gas chamber; second means for applying a voltage between the first and second pumping electrodes to activate the oxygen pumping cell; a sensor cell having 1) a second solid electrolyte member, 2) a first sensor electrode, and 3) a second sensor electrode, the second solid electrolyte member having an oxygen-ion conductivity, the first sensor electrode being exposed in the measurement gas chamber and extending on a first surface of the second solid electrolyte member, the first sensor electrode having an oxidizing activity with respect to the specific component of the measurement gas which is lower than the oxidizing activity of the first pumping electrode, the second sensor electrode being exposed to a reference gas and extending on a second surface of the second solid electrolyte member; third means for detecting an oxygen-ion current in the oxygen pumping cell when the second means applies the voltage between the first and second pumping electrodes; fourth means for applying a voltage between the first and second sensor electrodes; fifth means for detecting an oxygen-ion current in the sensor cell when the fourth means applies the voltage between the first and second sensor electrodes; and sixth means for detecting a concentration of the specific component of the measurement gas from a relation between the oxygen-ion currents detected by the third and fifth means.

A fourth aspect of this invention provides a method of detecting a gas concentration which is implemented in a gas sensor comprising a measurement gas chamber, an oxygen pumping cell having a pumping electrode which is exposed in the measurement gas chamber and has an oxidizing activity with respect to a specific component of a measurement gas, and a sensor cell having a sensor electrode which is exposed in the measurement gas chamber and has an oxidizing activity with respect to the specific component of the measurement gas, wherein the oxidizing activity of the sensor electrode is lower than that of the pumping electrode. The method comprises the steps of introducing the measurement gas into the measurement gas chamber under a prescribed diffusion resistance; applying a voltage to the oxygen pumping cell; applying a voltage to the sensor cell; detecting an oxygen-ion current in the oxygen pumping cell; detecting an oxygen-ion current in the sensor cell; and detecting a concentration of the specific component of the measurement gas from a relation between the detected oxygen-ion current in the oxygen pumping cell and the detected oxygen-ion current in the sensor cell.

DETAILED DESCRIPTION OF THE INVENTION

A prior-art hydrocarbon gas sensor will be explained below for a better understanding of this invention.

Figure 1:
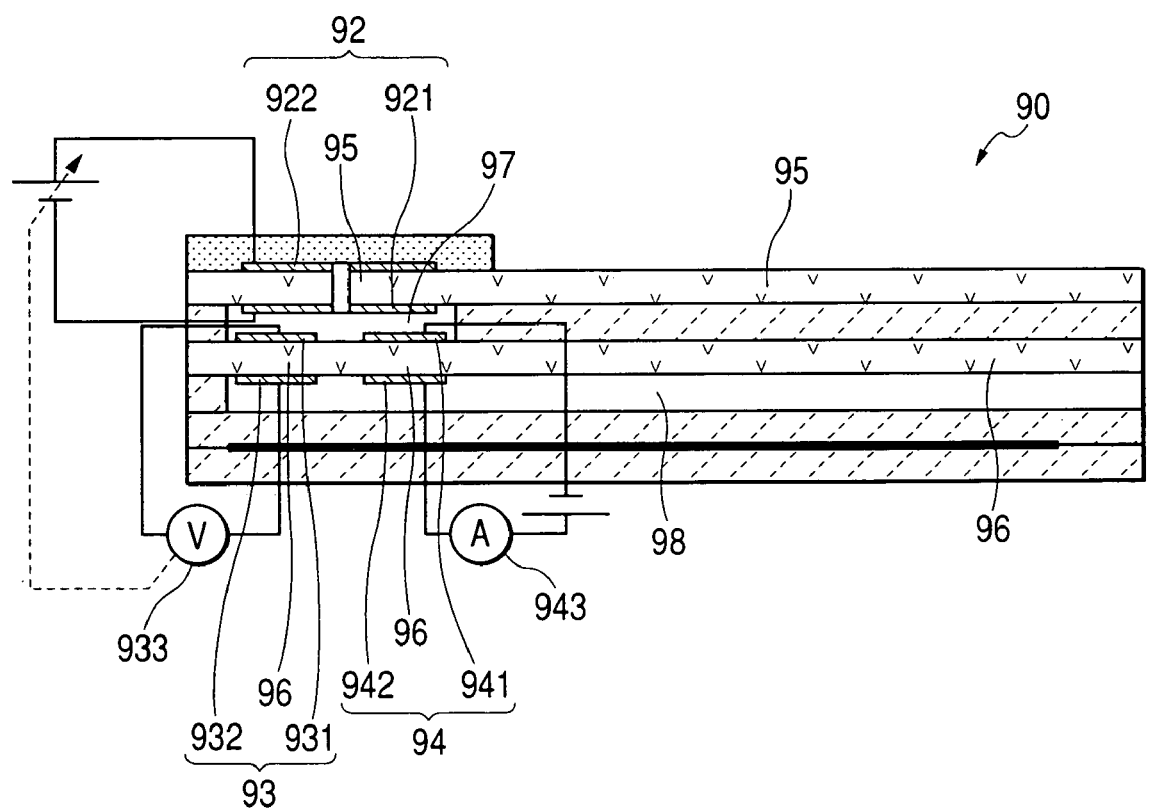
FIG. 1 is a sectional diagram of a prior-art hydrocarbon gas sensor.

FIG. 1 shows a prior-art hydrocarbon gas sensor 90 designed to measure the concentration of hydrocarbon in exhaust gas produced by an internal combustion engine (see U.S. Pat. No. 5,985,118). As shown in FIG. 1, the prior-art gas sensor 90 includes a monitor cell 93 and a sensor cell 94. The monitor cell 93 has a solid electrolyte member 96 and a pair of electrodes 931 and 932. The solid electrolyte member 96 is sandwiched between the electrodes 931 and 932. The electrodes 931 and 932 are opposed to each other. The electrode 931 which constitutes a measurement-gas-side electrode is active to hydrocarbon gas. The sensor cell 94 has the solid electrolyte member 96 and a pair of electrodes 941 and 942. The solid electrolyte member 96 is sandwiched between the electrodes 941 and 942. The electrodes 941 and 942 are opposed to each other. The electrode 941 which constitutes a measurement-gas-side electrode is inactive to hydrocarbon gas.

The prior-art gas sensor 90 in FIG. 1 includes a chamber 97 filled with a measurement gas. The measurement-gas-side electrode 931 in the monitor cell 93, and the measurement-gas-side electrode 941 in the sensor cell 94 are exposed to the measurement gas in the measurement gas chamber 97. The prior-art gas sensor 90 in FIG. 1 has a chamber 98 filled with a reference gas. The other electrode 932 in the monitor cell 93, and the other electrode 942 in the sensor cell 94 are exposed to the reference gas in the reference gas chamber 98.

The prior-art gas sensor 90 in FIG. 1 includes a pumping cell 92 for adjusting the oxygen concentration in the measurement gas within the measurement gas chamber 97. The pumping cell 92 has a solid electrolyte member 95 and a pair of electrodes 921 and 922. The solid electrolyte member 95 is sandwiched between the electrodes 921 and 922. The electrodes 921 and 922 are opposed to each other.

During operation of the prior-art gas sensor 90 in FIG. 1, an exhaust gas is introduced into the measurement gas chamber 97 as a measurement gas while a reference gas having a predetermined constant oxygen concentration is introduced into the reference gas chamber 98. Since the measurement-gas-side electrode 931 in the monitor cell 93 is active to hydrocarbon gas, hydrocarbon in the measurement gas reacts with oxygen therein when contacting the measurement-gas-side electrode 931. In other words, oxygen in the measurement gas adjoining the measurement-gas-side electrode 931 is consumed. Accordingly, there occurs a difference in oxygen concentration between the measurement gas adjoining the measurement-gas-side electrode 931 and the reference gas adjoining the other electrode 932 in the monitor cell 93. The oxygen-concentration difference causes an electromotive force between the electrodes 931 and 932. A voltage detector 933 senses the voltage between the electrodes 931 and 932 which depends on the electromotive force. The sensed voltage indicates the oxygen concentration in the measurement gas adjoining the measurement-gas-side electrode 931. In this way, the monitor cell 93 detects the oxygen concentration in the measurement gas adjoining the measurement-gas-side electrode 931 which is active to hydrocarbon gas. A voltage applied to the pumping cell 92 is controlled so that the oxygen concentration detected by the monitor cell 93 will be constant.

Since the measurement-gas-side electrode 941 in the sensor cell 94 is inactive to hydrocarbon gas, hydrocarbon in the measurement gas hardly reacts with oxygen therein when contacting the measurement-gas-side electrode 941. A voltage is applied between the electrodes 941 and 942 in the sensor cell 94, and an electric current flowing in the sensor cell 94 which results from an oxygen-ion transfer is sensed by a current detector 943. The sensed current indicates the oxygen concentration in the measurement gas adjoining the measurement-gas-side electrode 941. In this way, the sensor cell 94 detects the oxygen concentration in the measurement gas adjoining the measurement-gas-side electrode 941 which is inactive to hydrocarbon gas. The oxygen concentration detected by the monitor cell 93 and the oxygen concentration detected by the sensor cell 94 are used to estimate the hydrocarbon gas concentration in the measurement gas.

In the prior-art gas sensor 90 of FIG. 1, the monitor cell 93 detects the oxygen concentration by sensing the electromotive force occurring between the electrodes 931 and 932. On the other hand, the sensor cell 94 detects the oxygen concentration by sensing the oxygen-ion current flowing between the electrodes 941 and 942. Thus, the hydrocarbon gas concentration is derived from the two different state parameters, that is, the electromotive force and the oxygen-ion current. The two different state parameters exhibit different variations respectively as the environments of measurement of the hydrocarbon gas concentration change. Therefore, the result of the detection of the hydrocarbon gas concentration tends to have an error in the case where the measurement environments change. An example of the change in the measurement environments is a change in conditions of combustible components of the measurement gas or a change in the oxygen concentration in the measurement gas.

Basic Embodiments

According to a first basic embodiment of this invention, a gas sensor comprises a measurement gas chamber; first means for introducing a measurement gas into the measurement gas chamber under a prescribed diffusion resistance; an oxygen pumping cell for adjusting an oxygen concentration in the measurement gas chamber, the oxygen pumping cell having 1) a first solid electrolyte member, 2) a first pumping electrode, and 3) a second pumping electrode, the first solid electrolyte member having an oxygen-ion conductivity, the first pumping electrode being exposed in the measurement gas chamber and extending on a first surface of the first solid electrolyte member, the second pumping electrode extending on a second surface of the first solid electrolyte member and being separate from the measurement gas chamber; second means for applying a voltage between the first and second pumping electrodes to activate the oxygen pumping cell; an oxygen monitor cell having 1) a second solid electrolyte member, 2) a first monitor electrode, and 3) a second monitor electrode, the second solid electrolyte member having an oxygen-ion conductivity, the first monitor electrode being exposed in the measurement gas chamber and extending on a first surface of the second solid electrolyte member, the first monitor electrode having an oxidizing activity with respect to a specific component of the measurement gas, the second monitor electrode being exposed to a reference gas and extending on a second surface of the second solid electrolyte member; a sensor cell having 1) a third solid electrolyte member, 2) a first sensor electrode, and 3) a second sensor electrode, the third solid electrolyte member having an oxygen-ion conductivity, the first sensor electrode being exposed in the measurement gas chamber and extending on a first surface of the third solid electrolyte member, the first sensor electrode having an oxidizing activity with respect to the specific component of the measurement gas which is lower than the oxidizing activity of the first monitor electrode, the second sensor electrode being exposed to the reference gas and extending on a second surface of the third solid electrolyte member; third means for applying a voltage between the first and second monitor electrodes; fourth means for detecting an oxygen-ion current in the oxygen monitor cell when the third means applies the voltage between the first and second monitor electrodes; fifth means for applying a voltage between the first and second sensor electrodes; sixth means for detecting an oxygen-ion current in the sensor cell when the fifth means applies the voltage between the first and second sensor electrodes; and seventh means for detecting a concentration of the specific component of the measurement gas from a relation between the oxygen-ion currents detected by the fourth and sixth means.

In the gas sensor of the first basic embodiment of this invention, the first monitor electrode in the oxygen monitor cell and the first sensor electrode in the sensor cell are different in oxidizing activity with respect to the specific component of the measurement gas. A voltage is applied between the first and second monitor electrodes. A voltage is applied between the first and second sensor electrodes. An oxygen-ion current in the oxygen monitor cell is detected. An oxygen-ion current in the sensor cell is detected. A concentration of the specific component of the measurement gas is calculated from a relation between the detected oxygen-ion current in the oxygen monitor cell and the detected oxygen-ion current in the sensor cell.

The gas sensor of the first basic embodiment of this invention operates as follows. A measurement gas is introduced into the measurement gas chamber under a prescribed diffusion resistance. A voltage is applied between the first and second pumping electrodes to adjust an oxygen concentration in the measurement gas within the measurement gas chamber. Specifically, the oxygen concentration in the measurement gas is adjusted at a value suited for the detection of a concentration of the specific component of the measurement gas.

The oxygen concentration in the measurement gas which is adjusted by the oxygen pumping cell can be monitored by the oxygen monitor cell. The oxygen pumping cell controls the oxygen concentration detected by the oxygen monitor cell. Thus, the oxygen pumping cell adjusts the oxygen concentration in the measurement gas within the measurement gas chamber.

A voltage is applied between the first and second monitor electrodes. A voltage is applied between the first and second sensor electrodes.

The first monitor electrode, that is, the measurement-gas-side electrode, in the oxygen monitor cell has an oxidizing activity with respect to the specific component of the measurement gas. Therefore, when a voltage is applied between the first and second monitor electrodes, the specific component of the measurement gas reacts with oxygen in the measurement gas on the first monitor electrode (the measurement-gas-side electrode). An oxygen-ion current flowing in the oxygen monitor cell corresponds to an oxygen concentration resulting from the reaction of the specific component of the measurement gas with oxygen. The oxygen-ion current in the oxygen monitor cell is detected.

The first sensor electrode, that is, the measurement-gas-side electrode, in the sensor cell has an oxidizing activity with respect to the specific component of the measurement gas which is lower than the oxidizing activity of the measurement-gas-side electrode in the oxygen monitor cell. Therefore, the amount of the specific component of the measurement gas which reacts with oxygen in the measurement gas on the measurement-gas-side electrode of the sensor cell when a voltage is applied between the first and second sensor electrodes is smaller than that on the measurement-gas-side electrode of the oxygen monitor cell. Accordingly, the oxygen concentration in the measurement gas adjoining the first sensor electrode is higher than that in the measurement gas adjoining the first monitor electrode. An oxygen-ion current flowing in the sensor cell corresponds to the higher oxygen concentration. The oxygen-ion current in the sensor cell is detected.

The concentration of the specific component of the measurement gas is detected from a relation between the detected oxygen-ion current in the oxygen monitor cell and the detected oxygen-ion current in the sensor cell.

In the gas sensor of the first basic embodiment of this invention, the concentration of the specific component of the measurement gas is detected from a relation between the detected oxygen-ion current in the oxygen monitor cell and the detected oxygen-ion current in the sensor cell. Thus, the concentration of the specific component of the measurement gas is derived from the two state parameters of the same type, that is, the two oxygen-ion currents. The two same-type state parameters exhibit similar variations respectively as the environments of measurement of the specific-component concentration change. Therefore, the result of the detection of the specific-component concentration has hardly any error in the case where the measurement environments change. An example of the change in the measurement environments is a change in conditions of combustible components of the measurement gas or a change in the oxygen concentration in the measurement gas.

According to a second basic embodiment of this invention, a method of detecting a gas concentration is implemented in a gas sensor comprising a measurement gas chamber, an oxygen pumping cell having a pumping electrode exposed in the measurement gas chamber, an oxygen monitor cell having a monitor electrode which is exposed in the measurement gas chamber and has an oxidizing activity with respect to a specific component of a measurement gas, and a sensor cell having a sensor electrode which is exposed in the measurement gas chamber and has an oxidizing activity with respect to the specific component of the measurement gas, wherein the oxidizing activity of the sensor electrode is lower than that of the monitor electrode. The method comprises the steps of introducing the measurement gas into the measurement gas chamber under a prescribed diffusion resistance; applying a voltage to the oxygen monitor cell; applying a voltage to the sensor cell; detecting an oxygen-ion current in the oxygen monitor cell; detecting an oxygen concentration in the measurement gas chamber from the detected oxygen-ion current in the oxygen monitor cell; applying a voltage to the oxygen pumping cell; controlling the voltage applied to the oxygen pumping cell in response to the detected oxygen concentration in the measurement gas chamber to adjust the oxygen concentration in the measurement gas chamber; detecting an oxygen-ion current in the sensor cell; and detecting a concentration of the specific component of the measurement gas from a relation between the detected oxygen-ion current in the oxygen monitor cell and the detected oxygen-ion current in the sensor cell.

The method in the second basic embodiment of this invention utilizes the excellent performances of the gas sensor in the first basic embodiment thereof. Accordingly, the method in the second basic embodiment of this invention provides the result of the detection of the specific-component concentration which has hardly any error in the case where the environments of measurement of the specific-component concentration change.

According to a third basic embodiment of this invention, a gas sensor comprises a measurement gas chamber; first means for introducing a measurement gas into the measurement gas chamber under a prescribed diffusion resistance; an oxygen pumping cell for adjusting an oxygen concentration in the measurement gas chamber, the oxygen pumping cell having 1) a first solid electrolyte member, 2) a first pumping electrode, and 3) a second pumping electrode, the first solid electrolyte member having an oxygen-ion conductivity, the first pumping electrode being exposed in the measurement gas chamber and extending on a first surface of the first solid electrolyte member, the first pumping electrode having an oxidizing activity with respect to a specific component of the measurement gas, the second pumping electrode extending on a second surface of the first solid electrolyte member and being separate from the measurement gas chamber; second means for applying a voltage between the first and second pumping electrodes to activate the oxygen pumping cell; a sensor cell having 1) a second solid electrolyte member, 2) a first sensor electrode, and 3) a second sensor electrode, the second solid electrolyte member having an oxygen-ion conductivity, the first sensor electrode being exposed in the measurement gas chamber and extending on a first surface of the second solid electrolyte member, the first sensor electrode having an oxidizing activity with respect to the specific component of the measurement gas which is lower than the oxidizing activity of the first pumping electrode, the second sensor electrode being exposed to a reference gas and extending on a second surface of the second solid electrolyte member; third means for detecting an oxygen-ion current in the oxygen pumping cell when the second means applies the voltage between the first and second pumping electrodes; fourth means for applying a voltage between the first and second sensor electrodes; fifth means for detecting an oxygen-ion current in the sensor cell when the fourth means applies the voltage between the first and second sensor electrodes; and sixth means for detecting a concentration of the specific component of the measurement gas from a relation between the oxygen-ion currents detected by the third and fifth means.

The gas sensor in the third basic embodiment of this invention includes the oxygen pumping cell and the sensor cell. The oxygen pumping cell has the first pumping electrode exposed in the measurement gas chamber. The sensor cell has the first sensor electrode exposed in the measurement gas chamber. The first pumping electrode in the oxygen pumping cell and the first sensor electrode in the sensor cell are different in oxidizing activity with respect to the specific component of the measurement gas. A voltage is applied between the first and second pumping electrodes. A voltage is applied between the first and second sensor electrodes. An oxygen-ion current in the oxygen pumping cell is detected. An oxygen-ion current in the sensor cell is detected. A concentration of the specific component of the measurement gas is calculated from a relation between the detected oxygen-ion current in the oxygen pumping cell and the detected oxygen-ion current in the sensor cell.

The gas sensor of the third basic embodiment of this invention operates as follows. A measurement gas is introduced into the measurement gas chamber under a prescribed diffusion resistance. A voltage is applied between the first and second pumping electrodes to adjust an oxygen concentration in the measurement gas within the measurement gas chamber while monitoring the oxygen concentration. Specifically, the oxygen concentration in the measurement gas is adjusted at a value suited for the detection of a concentration of the specific component of the measurement gas.

A voltage is applied between the first and second pumping electrodes. A voltage is applied between the first and second sensor electrodes.

The first pumping electrode, that is, the measurement-gas-side electrode, in the oxygen pumping cell has an oxidizing activity with respect to the specific component of the measurement gas. Therefore, when a voltage is applied between the first and second pumping electrodes, the specific component of the measurement gas reacts with oxygen in the measurement gas on the first pumping electrode (the measurement-gas-side electrode). An oxygen-ion current flowing in the oxygen pumping cell corresponds to an oxygen concentration resulting from the reaction of the specific component of the measurement gas with oxygen. The oxygen-ion current in the oxygen pumping cell is detected.

The first sensor electrode, that is, the measurement-gas-side electrode, in the sensor cell has an oxidizing activity with respect to the specific component of the measurement gas which is lower than the oxidizing activity of the measurement-gas-side electrode in the oxygen pumping cell. Therefore, the amount of the specific component of the measurement gas which reacts with oxygen in the measurement gas on the measurement-gas-side electrode of the sensor cell when a voltage is applied between the first and second sensor electrodes is smaller than that on the measurement-gas-side electrode of the oxygen pumping cell. Accordingly, the oxygen concentration in the measurement gas adjoining the first sensor electrode is higher than that in the measurement gas adjoining the first pumping electrode. An oxygen-ion current flowing in the sensor cell corresponds to the higher oxygen concentration. The oxygen-ion current in the sensor cell is detected.

The concentration of the specific component of the measurement gas is detected from a relation between the detected oxygen-ion current in the oxygen pumping cell and the detected oxygen-ion current in the sensor cell.

In the gas sensor of the third basic embodiment of this invention, the concentration of the specific component of the measurement gas is detected from a relation between the detected oxygen-ion current in the oxygen pumping cell and the detected oxygen-ion current in the sensor cell. Thus, the concentration of the specific component of the measurement gas is derived from the two state parameters of the same type, that is, the two oxygen-ion currents. The two same-type state parameters exhibit similar variations respectively as the environments of measurement of the specific-component concentration change. Therefore, the result of the detection of the specific-component concentration has hardly any error in the case where the measurement environments change. An example of the change in the measurement environments is a change in conditions of combustible components of the measurement gas or a change in the oxygen concentration in the measurement gas.

According to a fourth basic embodiment of this invention, a method of detecting a gas concentration is implemented in a gas sensor comprising a measurement gas chamber, an oxygen pumping cell having a pumping electrode which is exposed in the measurement gas chamber and has an oxidizing activity with respect to a specific component of a measurement gas, and a sensor cell having a sensor electrode which is exposed in the measurement gas chamber and has an oxidizing activity with respect to the specific component of the measurement gas, wherein the oxidizing activity of the sensor electrode is lower than that of the pumping electrode. The method comprises the steps of introducing the measurement gas into the measurement gas chamber under a prescribed diffusion resistance; applying a voltage to the oxygen pumping cell; applying a voltage to the sensor cell; detecting an oxygen-ion current in the oxygen pumping cell; detecting an oxygen-ion current in the sensor cell; and detecting a concentration of the specific component of the measurement gas from a relation between the detected oxygen-ion current in the oxygen pumping cell and the detected oxygen-ion current in the sensor cell.

The method in the fourth basic embodiment of this invention utilizes the excellent performances of the gas sensor in the third basic embodiment thereof. Accordingly, the method in the fourth basic embodiment of this invention provides the result of the detection of the specific-component concentration which has hardly any error in the case where the environments of measurement of the specific-component concentration change.

In the first basic embodiment of this invention, the concentration of the specific component of the measurement gas may be detected from a difference between the oxygen-ion current in the sensor cell and the oxygen-ion current in the oxygen monitor cell. In this case, it is easy to detect the concentration of the specific component of the measurement gas.

Preferably, the gas sensor in the first basic embodiment of this invention further comprises eighth means for controlling the voltage between the first and second pumping electrodes in response to the oxygen-ion current detected by the fourth means so that the oxygen-ion current detected by the fourth means will be maintained at a desired value. In this case, the voltage applied to the oxygen pumping cell is feedback-controlled to maintain the oxygen-ion current in the oxygen monitor cell at the desired value. It is easy to adjust the oxygen concentration in the measurement gas chamber.

In the first basic embodiment of this invention, the specific component of the measurement gas may comprise hydrocarbon. In this case, the gas sensor can be used to detect a hydrocarbon concentration in the measurement gas.

In the first basic embodiment of this invention, the first monitor electrode, that is, the measurement-gas-side electrode, of the oxygen monitor cell may oxidize hydrocarbon.

In the first basic embodiment of this invention, the first monitor electrode, that is, the measurement-gas-side electrode, of the oxygen monitor cell may be higher than the first sensor electrode (the measurement-gas-side electrode) of the sensor cell in oxidizing activity with respect to hydrocarbon.

In the first basic embodiment of this invention, the first monitor electrode (the measurement-gas-side electrode) of the oxygen monitor cell may be higher than the first sensor electrode (the measurement-gas-side electrode) of the sensor cell in oxidizing activity with respect to hydrocarbon different from methane. In this case, the amount of hydrocarbon different from methane in the measurement gas which reacts with oxygen therein on the measurement-gas-side electrode of the oxygen monitor cell is greater than that on the measurement-gas-side electrode of the sensor cell. Thus, the gas sensor can selectively detect the concentration of hydrocarbon different from methane in the measurement gas.

The gas sensor in the first basic embodiment of this invention may further comprise eighth means for controlling the oxygen pumping cell to maintain an oxygen concentration, which results from reaction between hydrocarbon and oxygen on the first monitor cell, at a constant value. It is preferable that the first monitor electrode is higher than the first sensor electrode in oxidizing activity with respect to hydrocarbon, and the seventh means comprises means for detecting the concentration of hydrocarbon in the measurement gas from a difference between the oxygen-ion currents detected by the fourth and sixth means. In this case, it is possible to accurately detect the difference in oxygen concentration between the measurement gas adjoining the first monitor electrode and the measurement gas adjoining the first sensor electrode which depends on the hydrocarbon concentration in the measurement gas. Therefore, a high accuracy of detection of the hydrocarbon concentration can be provided.

In the first basic embodiment of this invention, the measurement-gas-side electrode of the sensor cell may be lower than the measurement-gas-side electrode of the oxygen monitor cell in oxidizing activity with respect to hydrocarbon including methane. In this case, the amount of hydrocarbon including methane in the measurement gas which reacts with oxygen therein on the measurement-gas-side electrode of the oxygen monitor cell is greater than that on the measurement-gas-side electrode of the sensor cell. Thus, the gas sensor can detect the concentration of hydrocarbon including methane in the measurement gas.

In the first basic embodiment of this invention, the measurement-gas-side electrode of the sensor cell may be lower than the measurement-gas-side electrode of the oxygen monitor cell in oxidizing activity with respect to hydrocarbon different from methane. In this case, the amount of hydrocarbon different from methane in the measurement gas which reacts with oxygen therein on the measurement-gas-side electrode of the oxygen monitor cell is greater than that on the measurement-gas-side electrode of the sensor cell. Thus, the gas sensor can selectively detect the concentration of hydrocarbon different from methane in the measurement gas.

According to the first basic embodiment of this invention, it is preferable that the measurement-gas-side electrode of the oxygen monitor cell and the measurement-gas-side electrode of the sensor cell are different in degree of oxygen adsorption so as to be different in oxidizing activity with respect to hydrocarbon.

Generally, in order to provide a weak oxygen adsorption, a measurement-gas-side electrode is made of material containing noble metal such as Pt, Pd, or Rh to which Au, Ag, or Cu is added. In order to provide a strong oxygen adsorption, a measurement-gas-side electrode is made of material containing noble metal such as Pt, Pd, or Rh to which metal easily forming oxide is added. An example of the metal easily forming oxide is Ti, Ta, or Nb. Accordingly, it is preferable that metal greater in heat of oxygen adsorption than noble metal is added to material for a measurement-gas-side electrode. Specifically, regarding the added metal, the heat of oxygen adsorption is preferably equal to or greater than about 80 kcal/mol.

In the first basic embodiment of this invention, it is preferable that each of the measurement-gas-side electrode of the oxygen monitor cell and the measurement-gas-side electrode of the sensor cell contains at least one of Pt, Pd, Rh, and Au as a main metal component, and also contains at least one of Ti, Ta, Nb, Al, W, Mo, Cr, Mn, Fe, Co, Ni, and Zr. In this case, the measurement-gas-side electrode of the oxygen monitor cell contains at least one of Pt, Pd, Rh, and Au as a main metal component, and has oxidizing activity with respect to hydrocarbon. When the measurement-gas-side electrode of the sensor cell contains at least one of Pt, Pd, Rh, and Au as a main metal component and also contains at least one of Ti, Ta, Nb, Al, W, Mo, Cr, Mn, Fe, Co, Ni, and Zr, the measurement-gas-side electrode of the sensor cell is lower than the measurement-gas-side electrode of the oxygen monitor cell in oxidizing activity with respect to hydrocarbon.

According to the first basic embodiment of this invention, it is preferable that the measurement-gas-side electrode of the oxygen monitor cell comprises an electrode material containing 99–80% Pt and 1–20% Au by weight, and the measurement-gas-side electrode of the sensor cell comprises either an electrode material containing 99–80% Pt and 1–20% $TiO_2$ or an electrode material containing 99–80% Pd and 1–20% $TiO_2$. Thereby, it is possible to selectively detect the concentration of hydrocarbon different from methane.

When the material for the measurement-gas-side electrode of the oxygen monitor cell contains less than 1% Au by weight, the oxidizing activity with respect to methane may be excessively high. When the material for the measurement-gas-side electrode of the oxygen monitor cell contains more than 20% Au by weight, the melting point is considerably low. Thus, it may be difficult to simultaneously fire a solid electrolyte member and the material for the measurement-gas-side electrode of the oxygen monitor cell.

When the material for the measurement-gas-side electrode of the sensor cell contains less than 1% $TiO_2$ by weight, the oxidizing activity with respect to hydrocarbon may be excessively high. When the material for the measurement-gas-side electrode of the sensor cell contains more than 20% $TiO_2$ by weight, the electric resistance may be excessively great.

More preferably, the material for the measurement-gas-side electrode for the oxygen monitor cell contains 5% or more Au by weight. More preferably, the material for the measurement-gas-side electrode for the sensor cell contains 10% or more $TiO_2$.

In the second basic embodiment of this invention, the concentration of the specific component of the measurement gas may be detected from a difference between the detected oxygen-ion current in the oxygen monitor cell and the detected oxygen-ion current in the sensor cell. In this case, the difference between the detected oxygen-ion currents corresponds to the concentration of the specific component, and it is easy to detect the concentration of the specific component.

According to the second basic embodiment of this invention, the voltage applied to the oxygen pumping cell may be controlled in response to the detected oxygen-ion current in the oxygen monitor cell so that the detected oxygen-ion current in the oxygen monitor cell will be maintained at a desired value. In this case, the voltage applied to the oxygen pumping cell is feedback-controlled to maintain the oxygen-ion current in the oxygen monitor cell at the desired value. It is easy to adjust the oxygen concentration in the measurement gas chamber.

In the second basic embodiment of this invention, the specific component of the measurement gas may comprise hydrocarbon. In this case, it is possible to detect a hydrocarbon concentration in the measurement gas. The measurement-gas-side electrode of the oxygen monitor cell has an oxidizing activity with respect to hydrocarbon. The measurement-gas-side electrode of the sensor cell is lower than the measurement-gas-side electrode of the oxygen monitor cell in oxidizing activity with respect to hydrocarbon.

According to the first and second basic embodiments of this invention, when the voltage applied to the oxygen pumping cell is controlled to maintain the oxygen-ion current in the oxygen monitor cell at a constant value, the oxygen-ion current in the sensor cell is equivalent to the difference between the oxygen-ion current in the sensor cell and the oxygen-ion current in the oxygen monitor cell. Thus, when the oxygen concentration measured by the oxygen monitor cell is controlled to be constant, the concentration of the specific component of the measurement gas can be accurately detected by measuring only the oxygen-ion current in the sensor cell.

In the third basic embodiment of this invention, the oxygen concentration in the measurement gas chamber may be controlled at a constant value in response to a relation between the voltage applied between the first and second pumping electrodes and the oxygen-ion current detected by the third means. Furthermore, the sixth means may comprise means for detecting the concentration of the specific component of the measurement gas from the oxygen-ion current detected by the fifth means. In this case, the oxygen-ion current in the sensor cell corresponds to the concentration of the specific component, and it is easy to detect the concentration of the specific component.

In the third basic embodiment of this invention, the specific component of the measurement gas may comprise hydrocarbon. In this case, the gas sensor can be used to detect a hydrocarbon concentration in the measurement gas.

According to the third basic embodiment of this invention, the first pumping cell (the measurement-gas-side electrode) of the oxygen pumping cell may be higher than the first sensor electrode (the measurement-gas-side electrode) of the sensor cell in oxidizing activity with respect to hydrocarbon.

In the third basic embodiment of this invention, it is preferable that the first pumping electrode (the measurement-gas-side electrode) of the oxygen pumping cell is higher than the first sensor electrode (the measurement-gas-side electrode) of the sensor cell in oxidizing activity with respect to hydrocarbon different from methane. In this case, the amount of hydrocarbon different from methane in the measurement gas which reacts with oxygen therein on the measurement-gas-side electrode of the oxygen pumping cell is greater than that on the measurement-gas-side electrode of the sensor cell. Thus, the gas sensor can selectively detect the concentration of hydrocarbon different from methane in the measurement gas.

According to the fourth basic embodiment of this invention, an oxygen concentration in the measurement gas chamber may be controlled at a constant value in response to a relation between the voltage applied to the oxygen pumping cell and the detected oxygen-ion current in the oxygen pumping cell. Furthermore, the concentration of the specific component of the measurement gas may be detected from the detected oxygen-ion current in the sensor cell. In this case, the oxygen-ion current in the sensor cell corresponds to the concentration of the specific component, and it is easy to detect the concentration of the specific component.

In the fourth basic embodiment of this invention, the specific component of the measurement gas may comprise hydrocarbon. In this case, it is possible to detect a hydrocarbon concentration in the measurement gas.

Each of the gas sensors in the first and third basic embodiments of this invention can be used as a hydrocarbon gas sensor provided in an exhaust system of an automotive engine. Furthermore, each of the gas sensors in the first and third basic embodiments of this invention can be used for air-to-fuel ratio control of an engine, catalyst control, catalyst-deterioration detection.

Each of the methods in the second and fourth basic embodiments of this invention can be used to detect a hydrocarbon concentration in an exhaust gas produced by an automotive engine. Furthermore, each of the methods in the second and fourth basic embodiments of this invention can be used for air-to-fuel ratio control of an engine, catalyst control, catalyst-deterioration detection.

First Specific Embodiment

Figure 2:
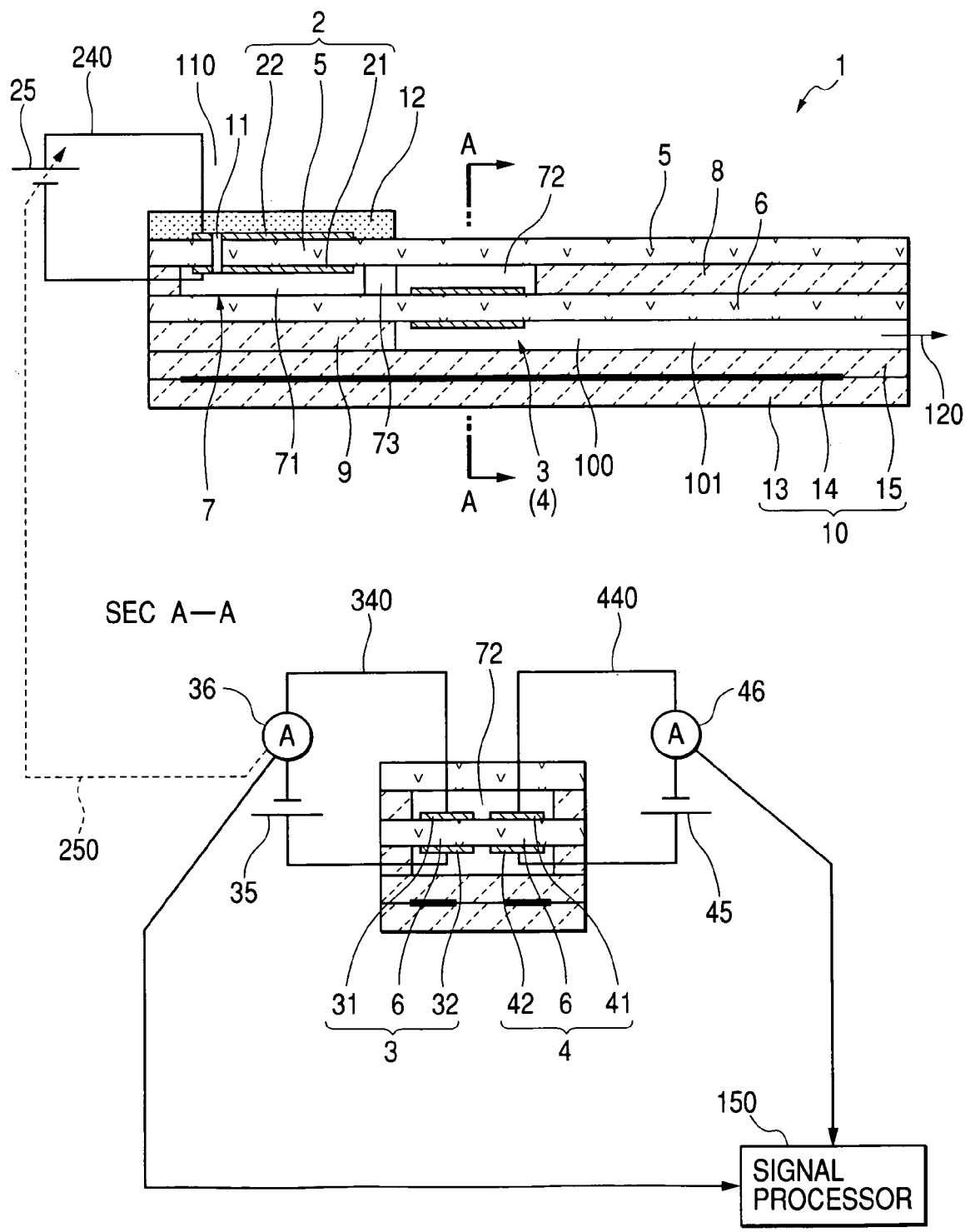
FIG. 2 is a sectional diagram of a gas sensor according to a first specific embodiment of this invention.

FIG. 2 shows a gas sensor 1 according to a first specific embodiment of this invention. The gas sensor 1 is designed to measure the concentration of hydrocarbon (HC) in a measurement gas such as an exhaust gas produced by an automotive engine. The detected HC concentration can be utilized in controlling the burning of an air-fuel mixture in the automotive engine.

As shown in FIG. 2, the gas sensor 1 includes a measurement gas chamber 7 into which a measurement gas (an exhaust gas) is introduced. The gas sensor 1 further includes an oxygen pumping cell 2, an oxygen monitor cell 3, and a sensor cell 4.

The oxygen pumping cell 2 has a solid electrolyte member 5 and a pair of electrodes 21 and 22. The electrodes 21 and 22 are provided on the lower and upper surfaces of the solid electrolyte member 5, respectively. The electrodes 21 and 22 are opposed to each other. The electrode 21 is exposed in the measurement gas chamber 7. The electrode 22 extends on an outer surface of the gas sensor 1 which is surrounded by the measurement gas.

The oxygen monitor cell 3 has a solid electrolyte member 6 and a pair of electrodes 31 and 32. The electrodes 31 and 32 are provided on the upper and lower surfaces of the solid electrolyte member 6, respectively. The electrodes 31 and 32 are opposed to each other. The electrode 31 is exposed in the measurement gas chamber 7. The electrode 32 is exposed in a reference gas chamber 100 into which an atmosphere is introduced as a reference gas having a predetermined constant oxygen concentration.

The sensor cell 4 has the solid electrolyte member 6 and a pair of electrodes 41 and 42. The electrodes 41 and 42 are provided on the upper and lower surfaces of the solid electrolyte member 6, respectively. The electrodes 41 and 42 are opposed to each other. The electrode 41 is exposed in the measurement gas chamber 7. The electrode 42 is exposed in the reference gas chamber 100.

The measurement-gas-side electrode 31 in the oxygen monitor cell 3 is active to hydrocarbon. Specifically, the measurement-gas-side electrode 31 has a sufficient oxidizing activity with respect to hydrocarbon. The hydrocarbon oxidizing activity of the measurement-gas-side electrode 41 in the sensor cell 4 is lower than that of the measurement-gas-side electrode 31 in the oxygen monitor cell 3. The measurement-gas-side electrode 41 in the sensor cell 4 may be inactive to hydrocarbon.

A voltage is applied between the electrodes 31 and 32 of the oxygen monitor cell 3. The applied voltage is chosen so that the oxygen monitor cell 3 will exhibit a limit current characteristic and hence an electric current flowing between the electrodes 31 and 32 and caused by an oxygen-ion transfer will depend on the oxygen concentration in a gas adjoining the electrode 31. In other words, the oxygen monitor cell 3 is operated as a limit-current-type cell.

A voltage is applied between the electrodes 41 and 42 of the sensor cell 4. The applied voltage is chosen so that the sensor cell 4 will exhibit a limit current characteristic and hence an electric current flowing between the electrodes 41 and 42 and caused by an oxygen-ion transfer will depend on the oxygen concentration in a gas adjoining the electrode 41. In other words, the sensor cell 4 is operated as a limit-current-type cell.

During operation of the gas sensor 1, the measurement gas is introduced into the measurement gas chamber 7 under a predetermined diffusion resistance. An oxygen-ion current flowing in the oxygen monitor cell 3 is detected while a voltage is applied between the electrodes 31 and 32 thereof. In addition, an oxygen-ion current flowing in the sensor cell 4 is detected while a voltage is applied between the electrodes 41 and 42 thereof. Normally, the oxygen pumping cell 2 serves to pump out oxygen from the measurement gas in the measurement gas chamber 7 toward an exterior of the gas sensor 1. The oxygen pumping cell 2 can transfer oxygen from the exterior of the gas sensor 1 to the measurement gas in the measurement gas chamber 7. The oxygen pumping cell 2 is driven by a voltage applied between the electrodes 21 and 22. The voltage applied to the oxygen pumping cell 2 is controlled in response to the detected oxygen-ion current in the oxygen monitor cell 3 so that the oxygen concentration in the measurement gas within the measurement gas chamber 7 will be adjusted. Specifically, a known circuit controls the oxygen-pumping-cell voltage in response to the detected oxygen-ion current in the oxygen monitor cell 3 on a feedback control basis. The feedback control of the oxygen-pumping-cell voltage is designed to regulate the detected oxygen-ion current in the oxygen monitor cell 3 at a desired value. The oxygen concentration in the measurement gas within the measurement gas chamber 7 is adjusted according to the feedback control of the oxygen-pumping-cell voltage. A specific-component concentration (a hydrocarbon concentration) in the measurement gas is detected or estimated on the basis of the relation between the detected oxygen-ion current in the oxygen monitor cell 3 and the detected oxygen-ion current in the sensor cell 4.

Figure 3:
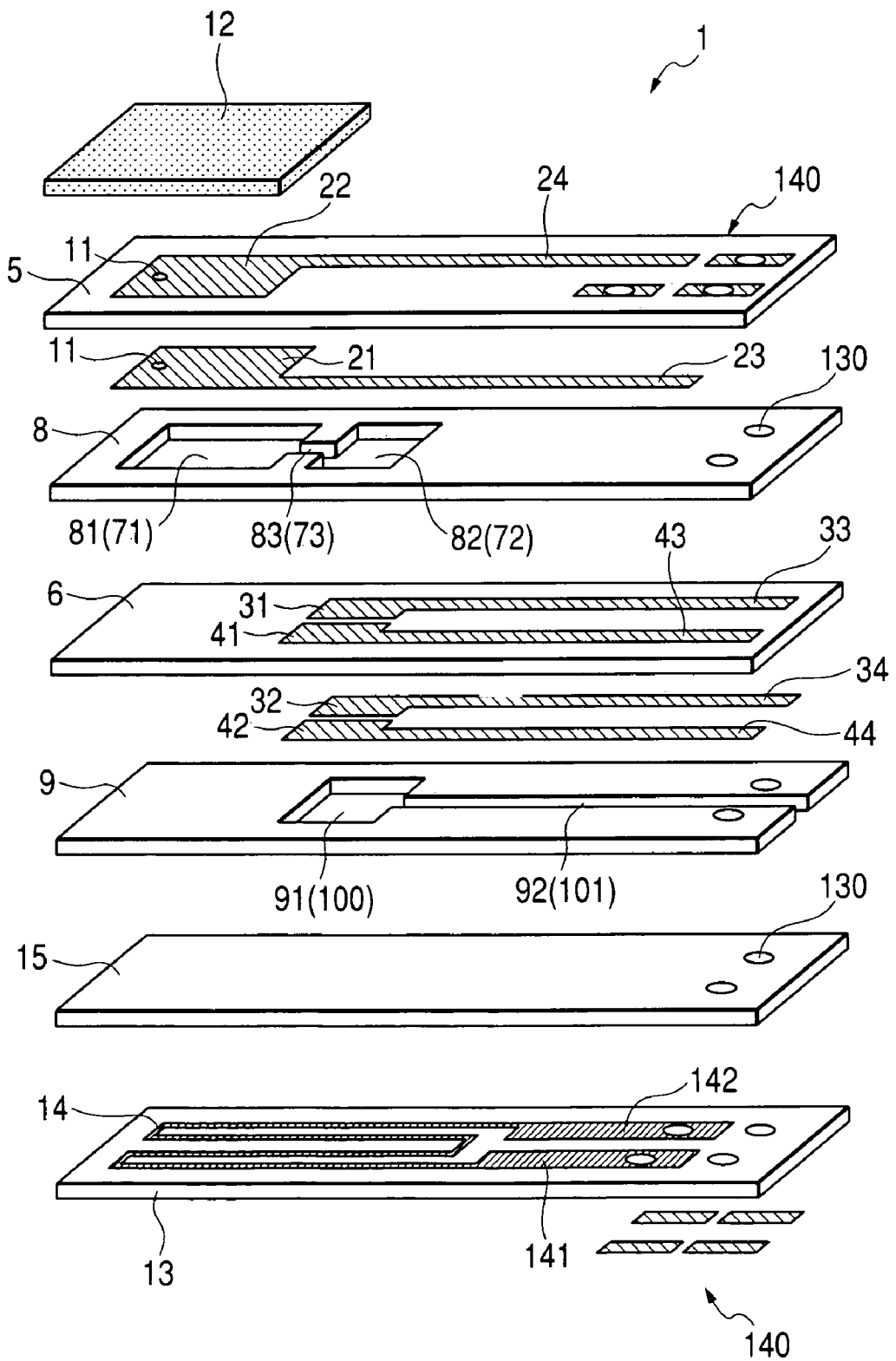
FIG. 3 is a perspective exploded view of the body of the gas sensor in FIG. 2.

As shown in FIGS. 2 and 3, the gas sensor 1 includes a laminate of a sheet-like solid electrolyte member 5, a sheet-like spacer 8, a sheet-like solid electrolyte member 6, a sheet-like spacer 9, and a ceramic heater 10 which are arranged in that order. The solid electrolyte member 5 is used in forming the oxygen pumping cell 2. The solid electrolyte member 6 is used in forming the oxygen monitor cell 3 and the sensor cell 4. The spacer 8 has an opening to form the measurement gas chamber 7. The spacer 9 has an opening to form the reference gas chamber 100. The ceramic heater 10 serves to heat the oxygen pumping cell 2, the oxygen monitor cell 3, and the sensor cell 4.

The solid electrolyte members 5 and 6 are made of an electrolyte having an oxygen-ion conductivity. Specifically, the solid electrolyte members 5 and 6 are made of, for example, zirconia or ceria. The spacers 8 and 9 are made of insulating material such as alumina.

An external space 110 surrounding a part of the gas sensor 1 is filled with the measurement gas. The measurement gas is introduced from the external space 110 into the measurement gas chamber 7. The measurement gas chamber 7 is divided into a first measurement gas chamber 71 and a second measurement gas chamber 72. The first measurement gas chamber 71 and the second measurement gas chamber 72 extend in an upstream side and a downstream side with respect to a measurement gas flow, respectively. The first measurement gas chamber 71 and the second measurement gas chamber 72 communicate with each other via a narrow passage or a restricted passage 73. The narrow passage 73 controls the rate of a flow of the measurement gas from the first measurement gas chamber 71 to the second measurement gas chamber 72. Thus, the narrow passage 73 provides a predetermined diffusion resistance to the measurement gas flow. The first measurement gas chamber 71, the second measurement gas chamber 72, and the narrow passage 73 are formed by holes 81, 82, and 83 in the spacer 8, respectively.

The solid electrolyte member 5 has a pinhole 11 via which the measurement gas is introduced from the external space 110 into the first measurement gas chamber 71. A porous protective layer 12 is provided on a part of the upper surface of the solid electrolyte member 5. An inlet of the pinhole 11 is covered by the porous protective layer 12. Also, the electrode 22 in the oxygen pumping cell 2 is covered by the porous protective layer 12. The pinhole 11 and the porous protective layer 12 control the rate of a flow of the measurement gas from the external space 110 to the first measurement gas chamber 71. Thus, the pinhole 11 and the porous protective layer 12 provide a predetermined diffusion resistance to the measurement gas flow. The effective cross-sectional area of the pinhole 11 is chosen so that the diffusion rate of the measurement gas introduced into the first measurement gas chamber 71 will be equal to a prescribed value. The porous protective layer 12 prevents the pinhole 11 from being clogged with foreign substances. Furthermore, the porous protective layer 12 prevents the electrodes 21 and 22 in the oxygen pumping cell 2, the measurement-gas-side electrode 31 in the oxygen monitor cell 3, and the measurement-gas-side electrode 41 in the sensor cell 4 from being contaminated or poisoned. The porous protective layer 12 is made of, for example, porous alumina.

It should be noted that the pinhole 11 may be replaced by a porous member made of, for example, porous alumina which introduces the measurement gas into the measurement gas chamber 7 while providing a predetermined diffusion resistance thereto.

An atmosphere having a predetermined constant oxygen concentration is introduced into the reference gas chamber 100 as a reference gas. The reference gas is utilized as a reference for detection of the hydrocarbon concentration in the measurement gas. The reference gas chamber 100 communicates via a passage 101 with an external space 120 surrounding a part of the gas sensor 1 and occupied by the atmosphere. The atmosphere enters the reference gas chamber 100 from the external space 120 via the passage 101. The reference gas chamber 100 and the passage 101 are formed by a hole 91 and a groove 92 in the spacer 9, respectively.

As previously mentioned, the oxygen pumping cell 2 is composed of the solid electrolyte member 5 and a pair of the electrodes 21 and 22. The solid electrolyte layer 5 is sandwiched between the electrodes 21 and 22. The electrodes 21 and 22 are opposed to each other. The electrode 21 extends on the lower surface of the solid electrolyte layer 5 which adjoins the spacer 8. The electrode 21 is exposed in the first measurement gas chamber 71. The electrode 22 extends on the upper surface of the solid electrolyte member 5 which adjoins the external space 110. The electrode 22 is exposed via the porous protective layer 12 to the measurement gas in the external space 110.

As previously mentioned, the oxygen monitor cell 3 is composed of the solid electrolyte member 6 and a pair of the measurement-gas-side electrode 31 and the reference-gas-side electrode 32. The solid electrolyte layer 6 is sandwiched between the electrodes 31 and 32. The electrodes 31 and 32 are opposed to each other. The measurement-gas-side electrode 31 extends on the upper surface of the solid electrolyte layer 6 which adjoins the spacer 8. The measurement-gas-side electrode 31 is exposed in the second measurement gas chamber 72. The reference-gas-side electrode 32 extends on the lower surface of the solid electrolyte member 6 which adjoins the spacer 9. The reference-gas-side electrode 32 is exposed in the reference gas chamber 100.

As previously mentioned, the sensor cell 4 is composed of the solid electrolyte member 6 and a pair of the measurement-gas-side electrode 41 and the reference-gas-side electrode 42. The solid electrolyte layer 6 is sandwiched between the electrodes 41 and 42. The electrodes 41 and 42 are opposed to each other. The measurement-gas-side electrode 41 extends on the upper surface of the solid electrolyte layer 6 which adjoins the spacer 8. The measurement-gas-side electrode 41 is exposed in the second measurement gas chamber 72. The reference-gas-side electrode 42 extends on the lower surface of the solid electrolyte member 6 which adjoins the spacer 9. The reference-gas-side electrode 42 is exposed in the reference gas chamber 100.

Preferably, in the second measurement gas chamber 72, the oxygen monitor cell 3 and the sensor cell 4 are juxtaposed or arranged in parallel with respect to a flow of the measurement gas. Alternatively, the oxygen monitor cell 3 and the sensor cell 4 may be arranged successively with respect to a flow of the measurement gas.

The electrode 21 in the oxygen pumping cell 2 and the measurement-gas-side electrode 41 in the sensor cell 4 include porous cermet electrodes containing Pt (platinum) and Au (gold) as main components to which Ti (titanium) is added. Preferably, the Au content or the Ti content of the materials for the electrodes 21 and 41 is in the range of 1 to 20% by weight. The electrode 21 in the oxygen pumping cell 2 and the measurement-gas-side electrode 41 in the sensor cell 4 are substantially inactive to hydrocarbon. In other words, each of the electrodes 21 and 41 has hardly any hydrocarbon oxidizing activity.

The measurement-gas-side electrode 31 in the oxygen monitor cell 3 includes a porous cermet electrode containing Pt (platinum) and Au (gold) as main components. Preferably, the Au content of the material for the electrode 31 is in the range of 1 to 20% by weight. The measurement-gas-side electrode 31 in the oxygen monitor cell 3 is active to hydrocarbon. In other words, the electrode 31 has a hydrocarbon oxidizing activity. The hydrocarbon oxidizing activity of the measurement-gas-side electrode 31 in the oxygen monitor cell 3 is higher than that of the measurement-gas-side electrode 41 in the sensor cell 4. Specifically, the electrode 31 is highly active to hydrocarbons except methane ($CH_4$).

The electrode 22 in the oxygen pumping cell 2, the reference-gas-side electrode 32 in the oxygen monitor cell 3, and the reference-gas-side electrode 42 in the sensor cell 4 include porous cermet electrodes containing Pt.

As best shown in FIG. 3, leads (wiring lines) 23, 24, 33, 34, 43, and 44 are formed integrally with the electrodes 21, 22, 31, 32, 41, and 42, respectively. The leads 23, 24, 33, 34, 43, and 44 are utilized for taking out electric signals from the electrodes 21, 22, 31, 32, 41, and 42, respectively. Preferably, an insulating layer made of, for example, alumina, is formed between the lead 23 and the solid electrolyte layer 5. Also, an insulating layer made of, for example, alumina, is formed between the lead 24 and the solid electrolyte layer 5. In addition, an insulating layer made of, for example, alumina, is formed between the lead 33 and the solid electrolyte layer 6. Also, an insulating layer made of, for example, alumina, is formed between the lead 34 and the solid electrolyte layer 6. Furthermore, an insulating layer made of, for example, alumina, is formed between the lead 43 and the solid electrolyte layer 6. Also, an insulating layer made of, for example, alumina, is formed between the lead 44 and the solid electrolyte layer 6.

The ceramic heater 10 includes a heater sheet 13, a heater electrode 14, and an insulating alumina layer 15. The heater sheet 13 is made of alumina. The heater electrode 14 is formed on the upper surface of the heater sheet 13 by patterning. The alumina layer 15 is superposed on the upper surface of the heater sheet 13 which has the heater electrode 14. Accordingly, the heater electrode 14 extends between the heater sheet 13 and the alumina layer 15. The alumina layer 15 adjacently extends below the spacer 9. Thus, the ceramic heater 10 adjoins the lower surface of the spacer 9. The heater electrode 14 uses a cermet containing Pt and ceramics such as alumina. The heater electrode 14 is heated when being fed with electric power from an external. The ceramic heater 10 operates to heat the oxygen pumping cell 2, the oxygen monitor cell 3, and the sensor cell 4 to temperatures at which the cells 2, 3, and 4 are active sufficiently for accurate detection of the specific-component concentration (the hydrocarbon concentration).

Sensor terminals 140 are provided on the upper and lower surfaces of the gas sensor 1. The solid electrolyte layer 5, the spacer 8, the spacer 9, the alumina layer 15, and the heater sheet 13 have through holes occupied by electric conductors. The electrodes 21 and 22 in the oxygen pumping cell 2, the electrodes 31 and 32 in the oxygen monitor cell 3, the electrodes 41 and 42 in the sensor cell 4, and opposite ends 141 and 142 of the heater electrode 14 are electrically connected with the sensor terminals 140 via the leads 23, 24, 33, 34, 43, and 44 and the electric conductors occupying the through holes 130. Lead lines are electrically connected with the sensor terminals 140 via connectors. The connections of the lead lines to the connectors are implemented by, for example, a crimping process, a soldering process, a brazing process, or a welding process. Electric signals and electric power can be transmitted between the gas sensor 1 (the cells 2, 3, and 4, and the ceramic heater 10) and an external circuit via the lead lines.

The solid electrolyte members 5 and 6, the spacers 8 and 9, the heater sheet 13, and the alumina layer 15 are made by suitable steps including the following steps. The materials for the solid electrolyte members 5 and 6, the spacers 8 and 9, the heater sheet 13, and the alumina layer 15 are shaped into desired sheet shapes by a DOCTOR BLADE method or an extrusion method.

The electrodes 21, 22, 31, 32, 41, and 42, the leads 23, 24, 33, 34, 43, and 44, and the sensor terminals 140 are made by, for example, screen printing.

The solid electrolyte members 5 and 6, the spacers 8 and 9, the porous protective layer 12, the heater sheet 13, and the alumina layer 15 are arranged in a laminate, being fired into a single body.

As shown in FIG. 2, a drive circuit 240 including a variable-voltage power supply 25 is electrically connected between the electrodes 21 and 22 of the oxygen pumping cell 2. The drive circuit 240 applies the voltage of the power supply 25 between the electrodes 21 and 22. Normally, the power supply 25 subjects the electrode 22 to a positive potential (a plus polarity) as shown in FIG. 2. In specified conditions, the power supply 25 subjects the electrode 21 to a positive potential (a plus polarity).

A drive and detection circuit 340 is electrically connected between the electrodes 31 and 32 of the oxygen monitor cell 3. The drive and detection circuit 340 includes a dc power supply 35 and a current detector 36 which are connected in series. The power supply 35 serves to apply a voltage between the electrodes 31 and 32. The current detector 36 senses an electric current equal to an oxygen-ion current flowing between the electrodes 31 and 32.

A drive and detection circuit 440 is electrically connected between the electrodes 41 and 42 of the sensor cell 4. The drive and detection circuit 440 includes a dc power supply 45 and a current detector 46 which are connected in series. The power supply 45 serves to apply a voltage between the electrodes 41 and 42. The current detector 46 senses an electric current equal to an oxygen-ion current flowing between the electrodes 41 and 42.

The power supplies 25, 35, and 45, and the current detectors 36 and 46 are connected with an external controller including a calculation means for implementing control and calculation processes. A signal representing the oxygen-ion current sensed by the current detector 36 is transmitted via a signal line 250 to the calculation means in the external controller. The calculation means in the external controller adjusts the voltage of the power supply 25 in response to the oxygen-ion current sensed by the current detector 36.

The external controller may include a signal processor 150 connected with the current detectors 36 and 46. The signal processor 150 receives signals representing the oxygen-ion currents sensed by the current detectors 36 and 46. The signal processor 150 includes a microcomputer having a combination of an input/output port, a processing section, a ROM, and a RAM. The signal processor 150 operates in accordance with a control program stored in the ROM. The control program is designed to enable the signal processor 150 to estimate the hydrocarbon concentration in the measurement gas from the relation between the oxygen-ion currents sensed by the current detectors 36 and 46. For example, the signal processor 150 calculates the difference between the oxygen-ion currents, and estimates the hydrocarbon concentration from the calculated difference. The signal processor 150 outputs a signal representative of the estimated hydrocarbon concentration.

The gas sensor 1 operates as follows. A measurement gas being an exhaust gas produced by the automotive engine is introduced into the first measurement gas chamber 71 from the external space 110 via the porous protective layer 12 and the pinhole 11. The power supply 25 applies a drive voltage between the electrodes 21 and 22 in the oxygen pumping cell 2, thereby causing the oxygen pumping cell 2 to implement a pumping action which transfers oxygen between the first measurement gas chamber 71 and the external space 110. The drive voltage applied between the electrodes 21 and 22, that is, the transfer of oxygen between the first measurement gas chamber 71 and the external space 110, is controlled to adjust the oxygen concentration in the measurement gas within the first measurement gas chamber 71.

When a drive voltage is applied between the electrodes 21 and 22 of the oxygen pumping cell 2 in a manner such that the electrode 22 is subjected to a positive potential (a plus polarity), oxygen molecules in the measurement gas within the first measurement gas chamber 71 are reduced into oxygen ions on the electrode 21. The oxygen ions flow from the electrode 21 toward the electrode 22 via the solid electrolyte layer 5 so that oxygen is pumped out from the measurement gas within the first measurement gas chamber 71. Therefore, the oxygen concentration in the measurement gas within the first measurement gas chamber 71 drops.

On the other hand, when a drive voltage is applied between the electrodes 21 and 22 of the oxygen pumping cell 2 in a manner such that the electrode 21 is subjected to a positive potential (a plus polarity), oxygen molecules and water vapor in the measurement gas within the external space 110 are reduced into oxygen ions and others on the electrode 22. The oxygen ions flow from the electrode 22 toward the electrode 21 via the solid electrolyte layer 5 so that oxygen is pumped into the measurement gas within the first measurement gas chamber 71. Therefore, the oxygen concentration in the measurement gas within the first measurement gas chamber 71 rises.

The oxygen pumping cell 2 implements such pumping actions, and thereby adjusts the oxygen concentration in the measurement gas within the first measurement gas chamber 71 at a value suited for the detection of the hydrocarbon concentration in the measurement gas. The oxygen-concentration-adjusted measurement gas is introduced from the first measurement gas chamber 71 into the second measurement gas chamber 72 via the narrow passage 73.

A voltage is applied between the electrodes 31 and 32 of the oxygen monitor cell 3. The applied voltage is chosen so that the oxygen monitor cell 3 will exhibit a limit current characteristic. The applied voltage is equal to, for example, 0.40 V. Similarly, a voltage is applied between the electrodes 41 and 42 of the sensor cell 4. The applied voltage is chosen so that the sensor cell 4 will exhibit a limit current characteristic. The applied voltage is equal to, for example, 0.40 V.

When a voltage is applied between the electrodes 31 and 32 of the oxygen monitor cell 3 in a manner such that the electrode 32 is subjected to a positive potential (a plus polarity) as shown in FIG. 2, oxygen molecules in the measurement gas within the second measurement gas chamber 72 are reduced into oxygen ions on the electrode 31. The oxygen ions flow from the electrode 31 toward the electrode 32 via the solid electrolyte layer 6. Thus, an oxygen-ion current flows between the electrodes 31 and 32. The drive voltage applied to the oxygen pumping cell 2 is adjusted in response to the oxygen-ion current in the oxygen monitor cell 3 on a feedback control basis so that the oxygen-ion current in the oxygen monitor cell 3 will be maintained at a prescribed constant value (equal to, for example, 0.5 $\mu$A).

The measurement-gas-side electrode 31 in the oxygen monitor cell 3 has a high hydrocarbon oxidizing activity. Therefore, on the electrode 31, hydrocarbon in the measurement gas within the second measurement gas chamber 72 reacts with oxygen therein. Accordingly, oxygen in the measurement gas adjoining the electrode 31 is consumed. Thus, the oxygen-ion current in the oxygen monitor cell 3 corresponds to the oxygen concentration in the measurement gas adjoining the electrode 31, that is, the oxygen concentration resulting from the reaction between hydrocarbon and oxygen or the consumption of oxygen.

When a voltage is applied between the electrodes 41 and 42 of the sensor cell 4 in a manner such that the electrode 42 is subjected to a positive potential (a plus polarity) as shown in FIG. 2, oxygen molecules in the measurement gas within the second measurement gas chamber 72 are reduced into oxygen ions on the electrode 41. The oxygen ions flow from the electrode 41 toward the electrode 42 via the solid electrolyte layer 6. Thus, an oxygen-ion current flows between the electrodes 41 and 42.

The measurement-gas-side electrode 41 in the sensor cell 4 has hardly any hydrocarbon oxidizing activity. Therefore, the amount of hydrocarbon in the measurement gas within the second measurement gas chamber 72 which reacts with oxygen therein on the electrode 41 is smaller than that on the electrode 31 of the oxygen monitor cell 3. Oxygen in the measurement gas adjoining the electrode 41 is hardly consumed. Thus, the oxygen concentration in the measurement gas adjoining the electrode 41 is higher than that in the measurement gas adjoining the electrode 31. The oxygen-ion current in the sensor cell 4 corresponds to the higher oxygen concentration.

As previously mentioned, the oxygen pumping cell 2 is controlled so that the oxygen-ion current in the oxygen monitor cell 3 will be maintained at the prescribed constant value. Thus, the oxygen concentration in the measurement gas adjoining the electrode 31, that is, the oxygen concentration resulting from the reaction between hydrocarbon and oxygen or the consumption of oxygen, is controlled at a constant level. When being compared with the oxygen-ion current in the oxygen monitor cell 3, the oxygen-ion current in the sensor cell 4 indicates the hydrocarbon concentration in the measurement gas within the second measurement gas chamber 72. Accordingly, the hydrocarbon concentration in the measurement gas is detected by measuring the oxygen-ion current in the sensor cell 4 while considering the relation between the oxygen-ion current in the sensor cell 4 and the oxygen-ion current in the oxygen monitor cell 3.

The current detectors 36 and 46 sense the oxygen-ion currents in the oxygen monitor cell 3 and the sensor cell 4, respectively. The hydrocarbon concentration in the measurement gas is detected on the basis of the oxygen-ion currents sensed by the current detectors 36 and 46. Thus, the hydrocarbon gas concentration is derived from the two state parameters of the same type, that is, the two oxygen-ion currents. The two same-type state parameters exhibit similar variations respectively as the environments of measurement of the hydrocarbon gas concentration change. Therefore, the result of the detection of the hydrocarbon gas concentration has hardly any error in the case where the measurement environments change. An example of the change in the measurement environments is a change in conditions of combustible components of the measurement gas or a change in the oxygen concentration in the measurement gas.

First experiments were performed on the gas sensor 1 and a comparative gas sensor. During the first experiments, each of methane ($CH_4$), propylene ($C_3H_6$), and ethylene ($C_2H_4$) being combustible gases was used as hydrocarbon in the measurement gas. The oxygen-ion current in the sensor cell 4 was measured as a sensor cell current ($\mu$A) while the hydrocarbon concentration (ppm) in the measurement gas was varied.

The oxygen concentration in the measurement gas was set to a constant value (0.001%). The measurement gas except hydrocarbon and oxygen consisted of nitrogen. The methane ($CH_4$) concentration, the propylene ($C_3H_6$) concentration, or the ethylene ($C_2H_4$) concentration in the measurement gas was varied between 0 to 500 ppm relative to the nitrogen concentration therein.

The measurement gas was introduced into the measurement gas chamber 7 of the gas sensor 1, and the oxygen-ion current in the sensor cell 4 was measured as a sensor cell current ($\mu$A).

A comparative gas sensor was prepared. The comparative gas sensor was designed so that an oxygen monitor cell detected an oxygen concentration from an electromotive force. The measurement gas was introduced into a measurement gas chamber of the comparative gas sensor, and an oxygen-ion current in a sensor cell was measured as a sensor cell current ($\mu$A).

Figure 4:
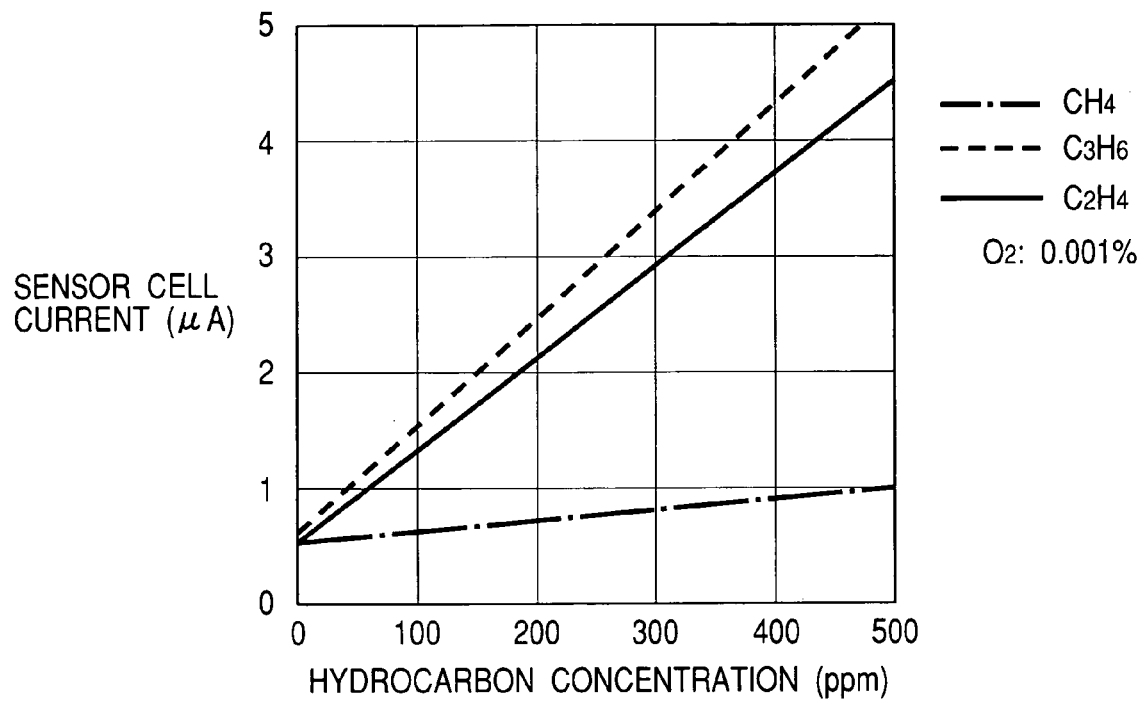
FIG. 4 is a diagram of the relation among a sensor cell current, a hydrocarbon concentration, and a hydrocarbon type which occurs in the gas sensor of FIG. 2.
Figure 5:
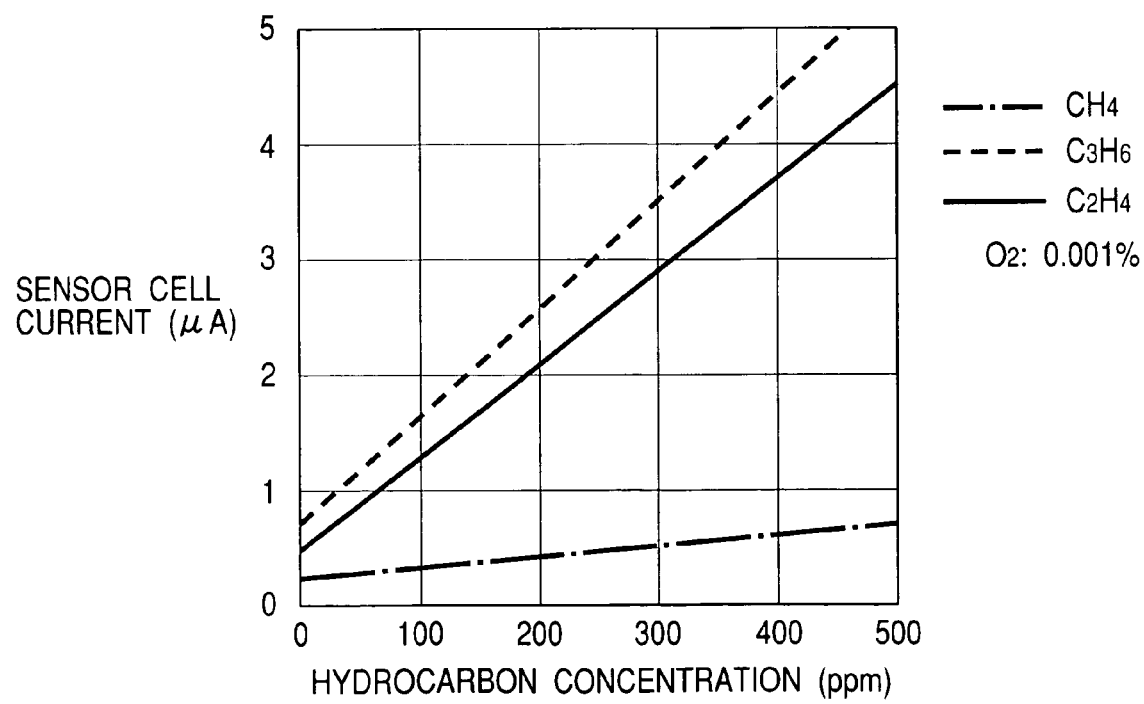
FIG. 5 is a diagram of the relation among a sensor cell current, a hydrocarbon concentration, and a hydrocarbon type which occurs in a comparative gas sensor.

FIG. 4 shows the relation among the measured sensor cell current, the methane ($CH_4$) concentration, the propylene ($C_3H_6$) concentration, and the ethylene ($C_2H_4$) concentration which was obtained by the first experiments on the gas sensor 1. FIG. 5 shows the relation among the measured sensor cell current, the methane ($CH_4$) concentration, the propylene ($C_3H_6$) concentration, and the ethylene ($C_2H_4$) concentration which was obtained by the first experiments on the comparative gas sensor. In the comparative gas sensor, the sensor cell current occurring at a hydrocarbon concentration of 0 ppm, that is, the offset sensor cell current, significantly changed depending on the type of hydrocarbon. On the other hand, in the gas sensor 1, the sensor cell current occurring at a hydrocarbon concentration of 0 ppm (that is, the offset sensor cell current) hardly changed depending on the type of hydrocarbon. As understood from the above-mentioned results of the first experiments, the gas sensor 1 can accurately detect the hydrocarbon concentration in the measurement gas even when the type of hydrocarbon changes.

Second experiments were performed on the gas sensor 1 and the comparative gas sensor. During the second experiments, ethylene ($C_2H_4$) was used as hydrocarbon in the measurement gas. The oxygen-ion current in the sensor cell 4 was measured as a sensor cell current ($\mu A$) while the hydrocarbon concentration (ppm) in the measurement gas was varied and also the oxygen concentration in the measurement gas was changed among 0.001%, 10%, and 20%.

The measurement gas except hydrocarbon and oxygen consisted of nitrogen. The ethylene ($C_2H_4$) concentration in the measurement gas was varied between 0 to 500 ppm relative to the nitrogen concentration therein.

The measurement gas was introduced into the measurement gas chamber 7 of the gas sensor 1, and the oxygen-ion current in the sensor cell 4 was measured as a sensor cell current ($\mu A$).

Similarly, the measurement gas was introduced into the measurement gas chamber of the comparative gas sensor, and the oxygen-ion current in the sensor cell was measured as a sensor cell current ($\mu A$).

Figure 6:
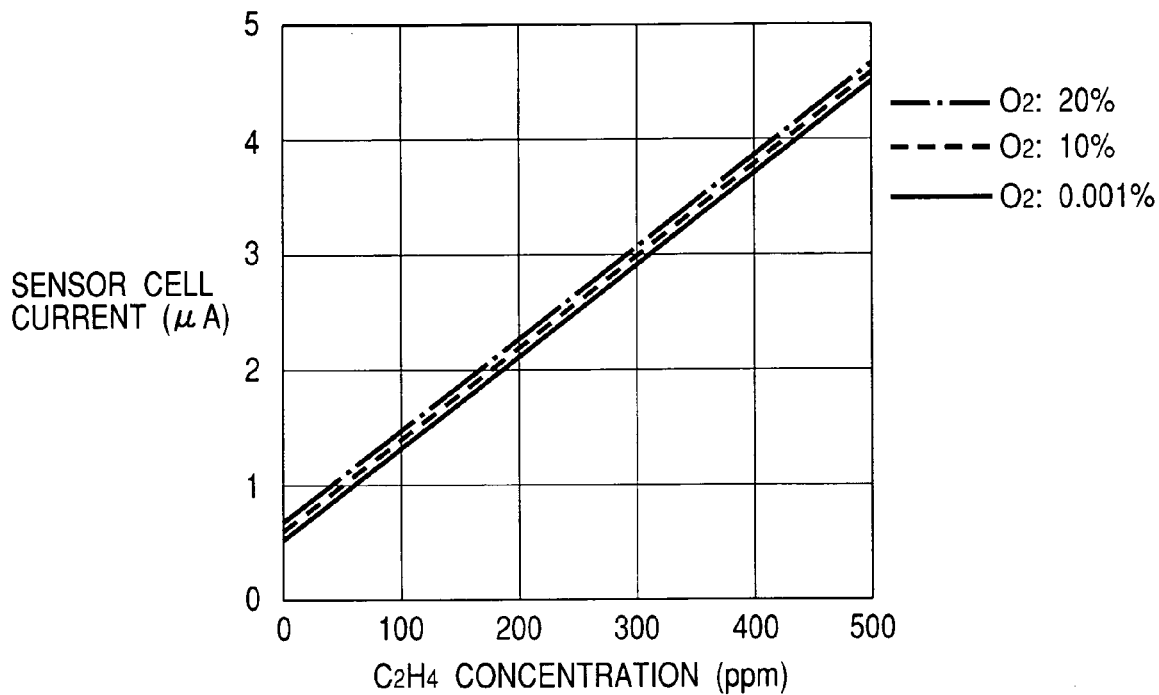
FIG. 6 is a diagram of the relation among a sensor cell current, a hydrocarbon concentration, and an oxygen concentration which occurs in the gas sensor of FIG. 2.
Figure 7:
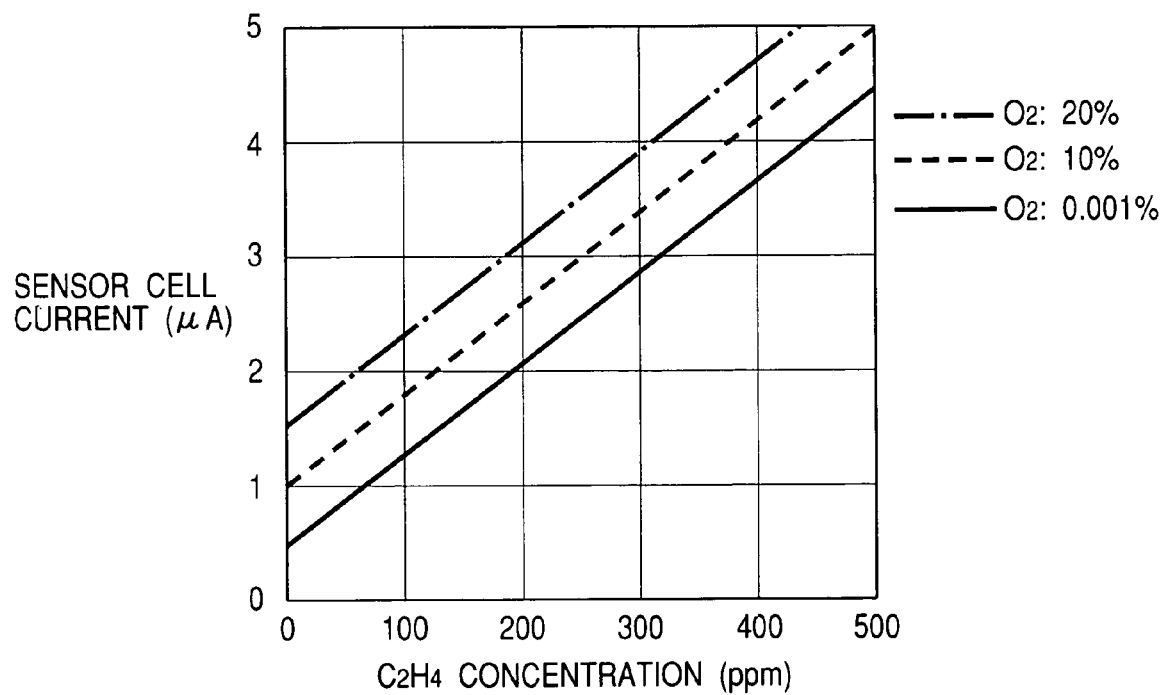
FIG. 7 is a diagram of the relation among a sensor cell current, a hydrocarbon concentration, and an oxygen concentration which occurs in the comparative gas sensor.

FIG. 6 shows the relation among the measured sensor cell current, the ethylene ($C_2H_4$) concentration, and the oxygen concentration which was obtained by the second experiments on the gas sensor 1. FIG. 7 shows the relation among the measured sensor cell current, the ethylene ($C_2H_4$) concentration, and the oxygen concentration which was obtained by the first experiments on the comparative gas sensor. In the comparative gas sensor, the sensor cell current occurring at a hydrocarbon concentration of 0 ppm, that is, the offset sensor cell current, significantly changed depending on the oxygen concentration. On the other hand, in the gas sensor 1, the sensor cell current occurring at a hydrocarbon concentration of 0 ppm (that is, the offset sensor cell current) hardly changed depending on the oxygen concentration. As understood from the above-mentioned results of the second experiments, the gas sensor 1 can accurately detect the hydrocarbon concentration in the measurement gas even when the oxygen concentration therein changes.

Second Specific Embodiment

A gas sensor 1 of a second specific embodiment of this invention is similar to that of the first specific embodiment thereof except for a design change mentioned hereafter.

In the gas sensor 1 of the second specific embodiment of this invention, the measurement-gas-side electrode 31 of the oxygen monitor cell 3 is active to hydrocarbon including methane ($CH_4$). Specifically, the measurement-gas-side electrode 31 has a sufficient oxidizing activity with respect to hydrocarbon including methane ($CH_4$). The hydrocarbon oxidizing activity of the measurement-gas-side electrode 41 in the sensor cell 4 is lower than that of the measurement-gas-side electrode 31 in the oxygen monitor cell 3.

Specifically, the measurement-gas-side electrode 31 in the oxygen monitor cell 3 includes a porous cermet electrode containing Pt (platinum). The electrode 31 is highly active to hydrocarbon including methane ($CH_4$). In other words, the electrode 31 has a high oxidizing activity with respect to hydrocarbon including methane ($CH_4$).

Experiments were performed on the gas sensor 1. During the experiments, each of methane ($CH_4$), propylene ($C_3H_6$), and ethylene ($C_2H_4$) being combustible gases was used as hydrocarbon in the measurement gas. The oxygen-ion current in the sensor cell 4 was measured as a sensor cell current ($\mu A$) while the hydrocarbon concentration (ppm) in the measurement gas was varied.

The oxygen concentration in the measurement gas was set to a constant value (0.001%). The measurement gas except hydrocarbon and oxygen consisted of nitrogen. The methane ($CH_4$) concentration, the propylene ($C_3H_6$) concentration, or the ethylene ($C_2H_4$) concentration in the measurement gas was varied between 0 to 500 ppm relative to the nitrogen concentration therein.

The measurement gas was introduced into the measurement gas chamber 7 of the gas sensor 1, and the oxygen-ion current in the sensor cell 4 was measured as a sensor cell current ($\mu A$).

Figure 8:
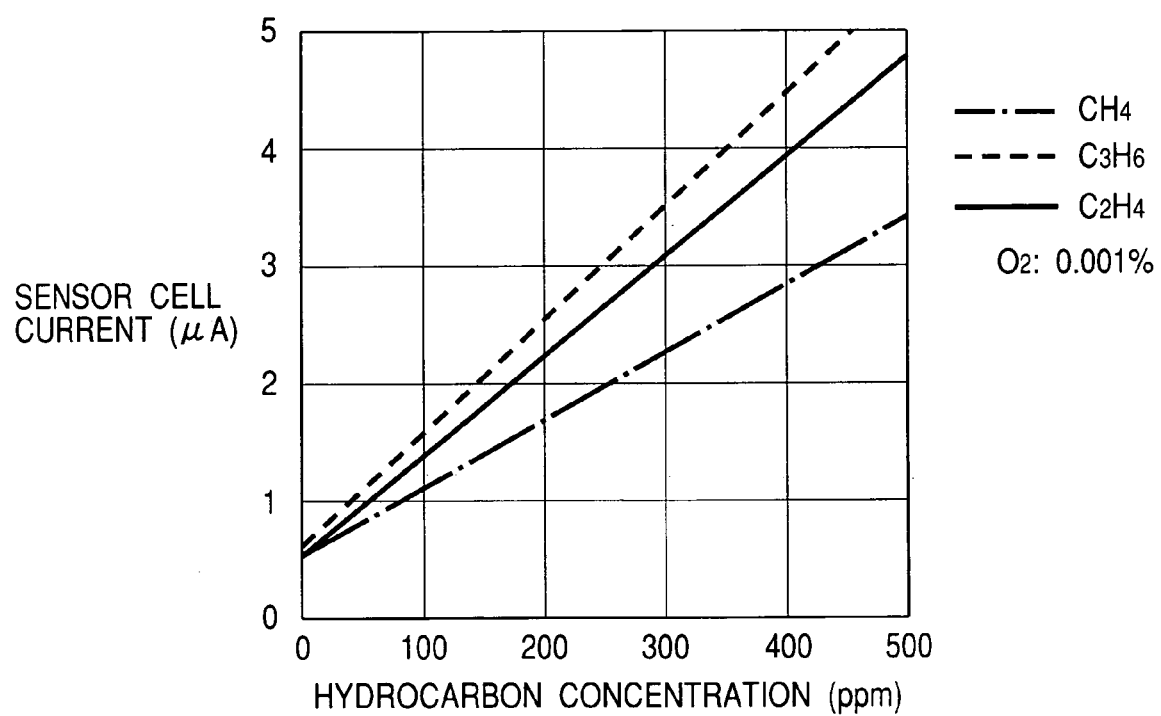
FIG. 8 is a diagram of the relation among a sensor cell current, a hydrocarbon concentration, and a hydrocarbon type which occurs in a gas sensor according to a second specific embodiment of this invention.

FIG. 8 shows the relation among the measured sensor cell current, the methane ($CH_4$) concentration, the propylene ($C_3H_6$) concentration, and the ethylene ($C_2H_4$) concentration which was obtained by the experiments on the gas sensor 1. The sensitivity of the gas sensor 1 with respect to methane ($CH_4$) is higher than that of the gas sensor in the first specific embodiment of this invention. In the gas sensor 1, the sensor cell current occurring at a hydrocarbon concentration of 0 ppm (that is, the offset sensor cell current) hardly changed depending on the type of hydrocarbon. As understood from the above-mentioned results of the experiments, the gas sensor 1 can accurately detect the hydrocarbon concentration in the measurement gas even when the type of hydrocarbon changes.

Third Specific Embodiment

Figure 9:
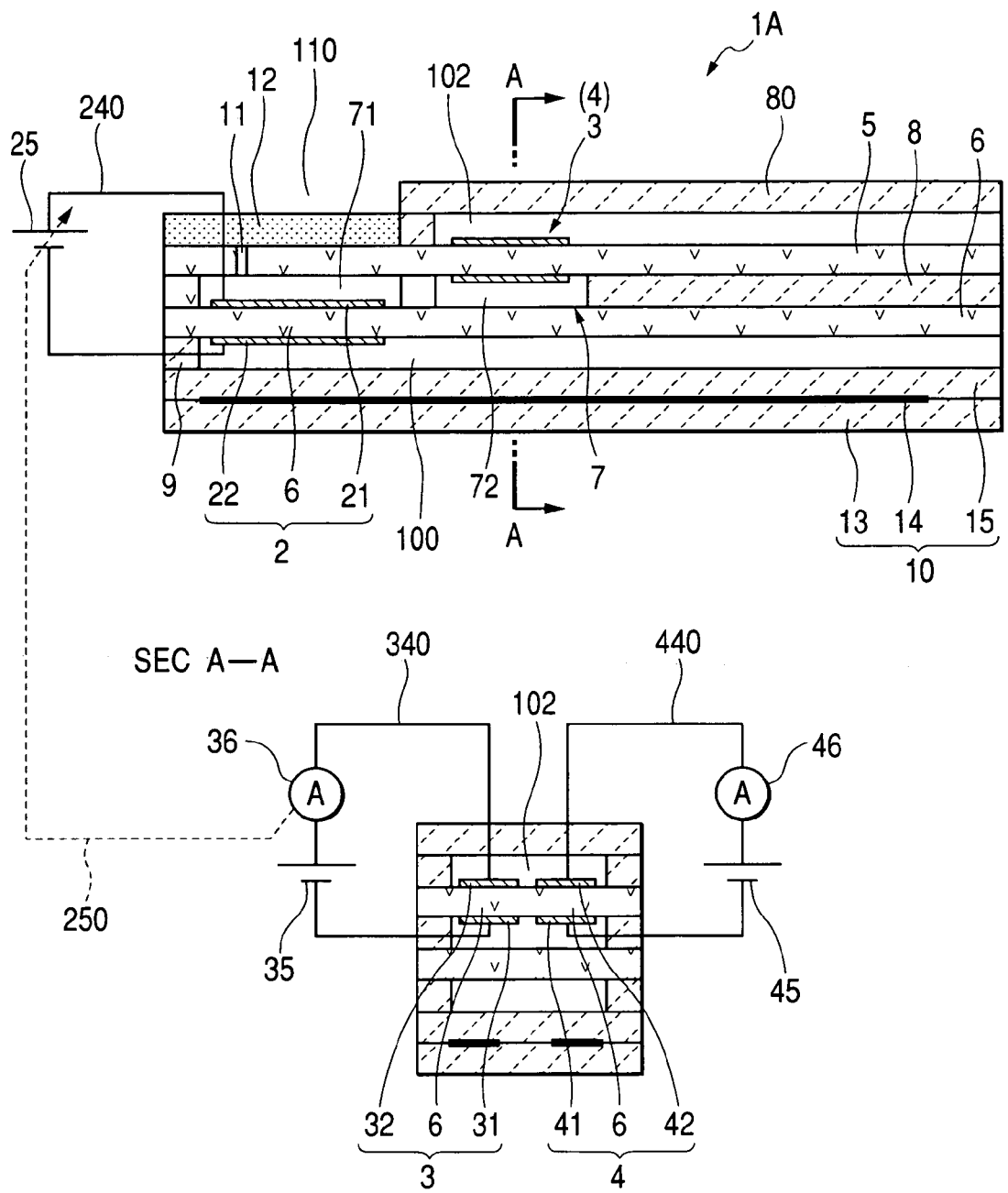
FIG. 9 is a sectional diagram of a gas sensor according to a third specific embodiment of this invention.

FIG. 9 shows a gas sensor 1A according to a third specific embodiment of this invention. The gas sensor 1A is similar to the gas sensor 1 (FIG. 2) except for design changes mentioned hereafter.

As shown in FIG. 9, the gas sensor 1A includes a measurement gas chamber 7 into which a measurement gas (an exhaust gas) is introduced. The measurement gas chamber 7 is divided into a first measurement gas chamber 71 and a second measurement gas chamber 72 which communicate with each other. The gas sensor 1A further includes an oxygen pumping cell 2, an oxygen monitor cell 3, and a sensor cell 4.

The oxygen pumping cell 2 has a solid electrolyte member 6 and a pair of electrodes 21 and 22. The electrodes 21 and 22 are provided on the upper and lower surfaces of the solid electrolyte member 6, respectively. The electrode 21 is exposed in the first measurement gas chamber 71. The electrode 22 is exposed in a reference gas chamber 100 into which an atmosphere is introduced as a reference gas having a predetermined constant oxygen concentration.

The oxygen monitor cell 3 has a solid electrolyte member 5 and a pair of electrodes 31 and 32. The electrodes 31 and 32 are provided on the upper and lower surfaces of the solid electrolyte member 5, respectively. The electrode 31 is exposed in the second measurement gas chamber 72. The electrode 32 is exposed in a reference gas chamber 102 into which the atmosphere is introduced as a reference gas having a predetermined constant oxygen concentration.

The sensor cell 4 has the solid electrolyte member 5 and a pair of electrodes 41 and 42. The electrodes 41 and 42 are provided on the lower and upper surfaces of the solid electrolyte member 5, respectively. The electrode 41 is exposed in the second measurement gas chamber 72. The electrode 42 is exposed in the reference gas chamber 102.

As shown in FIG. 9, the gas sensor 1A includes a laminate of a sheet-like spacer 80, a sheet-like solid electrolyte member 5, a sheet-like spacer 8, a sheet-like solid electrolyte member 6, a sheet-like spacer 9, and a ceramic heater 10 which are arranged in that order. The spacer 80 is superposed on a part of the upper surface of the solid electrolyte member 5. The reference gas chamber 102 is defined between the spacer 80 and the solid electrolyte member 5. The reference-gas-side electrode 32 of the oxygen monitor cell 3 and the reference-gas-side electrode 42 of the sensor cell 4 are exposed in the reference gas chamber 102. The solid electrolyte member 5 is used in forming the oxygen monitor cell 3 and the sensor cell 4. The solid electrolyte member 6 is used in forming the oxygen pumping cell 2.

The oxygen pumping cell 2 pumps and transfers oxygen between the measurement gas chamber 7 and the reference gas chamber 100, thereby adjusting the oxygen concentration in the measurement gas within the measurement gas chamber 7. Therefore, even in the case where the measurement gas introduced from the external space 110 lacks an oxygen source such as oxygen molecules and water vapor, the oxygen concentration in the measurement gas within the measurement gas chamber 7 can be adjusted by using oxygen in the reference gas within the reference gas chamber 100.

Preferably, in the second measurement gas chamber 72, the oxygen monitor cell 3 and the sensor cell 4 are juxtaposed or arranged in parallel with respect to a flow of the measurement gas.

The oxygen monitor cell 3 and the sensor cell 4 may be located in the first measurement gas chamber 71. In the first measurement gas chamber 71, the oxygen monitor cell 3 and the sensor cell 4 may be arranged successively with respect to a flow of the measurement gas.

The oxygen monitor cell 3 and the sensor cell 4 may be located in the first measurement gas chamber 71 and the second measurement gas chamber 72, respectively.

Fourth Specific Embodiment

Figure 10:
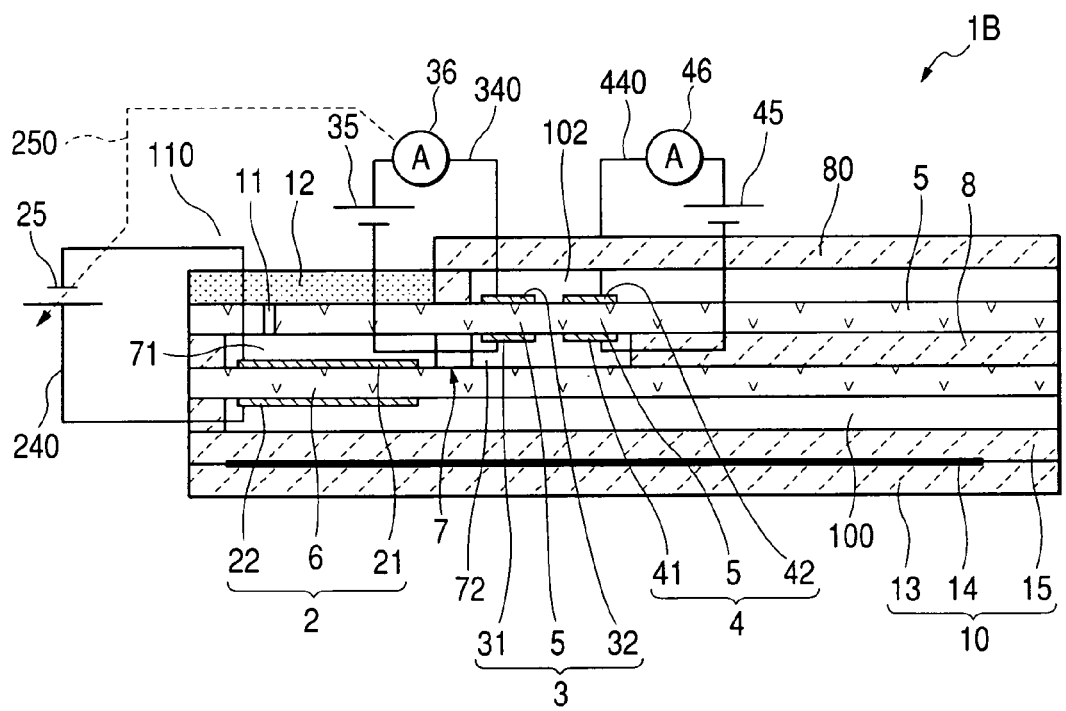
FIG. 10 is a sectional diagram of a gas sensor according to a fourth specific embodiment of this invention.

FIG. 10 shows a gas sensor 1B according to a fourth specific embodiment of this invention. The gas sensor 1B is similar to the gas sensor 1A (FIG. 9) except for a design change mentioned hereafter.

As shown in FIG. 10, in the second measurement gas chamber 72 of the gas sensor 1B, the oxygen monitor cell 3 and the sensor cell 4 are arranged successively with respect to a flow of the measurement gas.

Fifth Specific Embodiment

Figure 11:
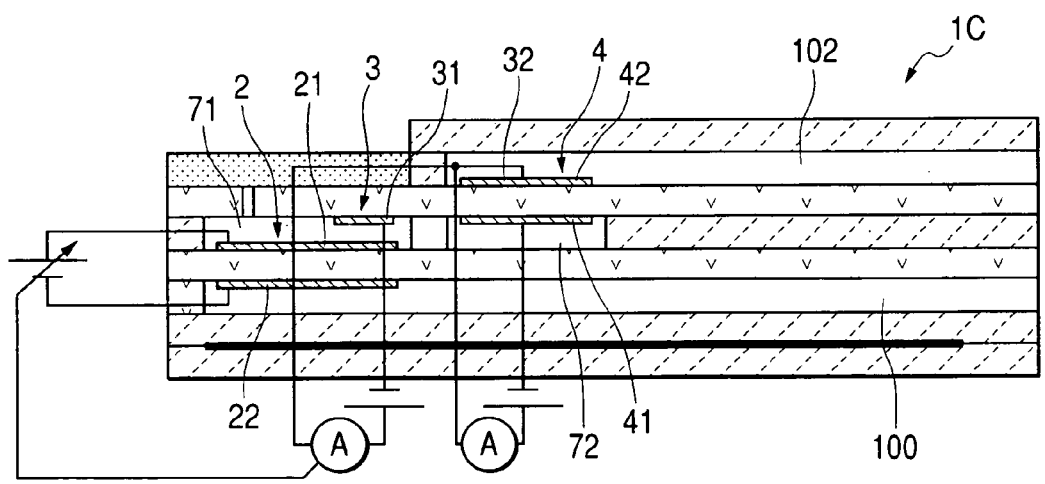
FIG. 11 is a sectional diagram of a gas sensor according to a fifth specific embodiment of this invention.

FIG. 11 shows a gas sensor 1C according to a fifth specific embodiment of this invention. The gas sensor 1C is similar to the gas sensor 1B (FIG. 10) except for design changes mentioned hereafter.

As shown in FIG. 11, the gas sensor 1C includes a common electrode which forms both the reference-gas-side electrode 32 of the oxygen monitor cell 3 and the reference-gas-side electrode 42 of the sensor cell 4. The measurement-gas-side electrode 31 of the oxygen monitor cell 3 is exposed in the first measurement gas chamber 71.

The electrode 21 of the oxygen pumping cell 2 is made of material preferably containing 98% Pt (platinum) and 2% Au (gold) by weight. The measurement-gas-side electrode 31 of the oxygen monitor cell 3 is made of material preferably containing 95% Pt and 5% Au by weight. The measurement-gas-side electrode 41 of the sensor cell 4 is made of material preferably containing 90% Pt and 10% $TiO_2$ (titanium dioxide) by weight. To provide a suitable gas conductivity, $ZrO_2$ may be added to each of the electrodes of the oxygen pumping cell 2, the oxygen monitor cell 3, and the sensor cell 4 by 10 weight %.

Experiments were performed on the gas sensor 1C. During the experiments, each of methane ($CH_4$), ethane ($C_2H_6$), propylene ($C_3H_6$), ethylene ($C_2H_4$), and butane ($C_4H_{10}$) being combustible gases was used as hydrocarbon in the measurement gas. The oxygen-ion current in the sensor cell 4 was measured as a sensor cell current ($\mu$A) while the hydrocarbon concentration (ppm) in the measurement gas was varied.

The measurement gas except hydrocarbon consisted of nitrogen and oxygen. The concentration of oxygen in the measurement gas relative to nitrogen was set to a constant value (5,000 ppm). The methane ($CH_4$) concentration, the ethane ($C_2H_6$) concentration, the propylene ($C_3H_6$) concentration, the ethylene ($C_2H_4$) concentration, or the butane ($C_4H_{10}$) concentration in the measurement gas was varied between 0 to 500 ppm relative to the nitrogen concentration therein.

The measurement gas was introduced into the measurement gas chamber 7 of the gas sensor 1C, and the oxygen-ion current in the sensor cell 4 was measured as a sensor cell current ($\mu$A).

Figure 12:
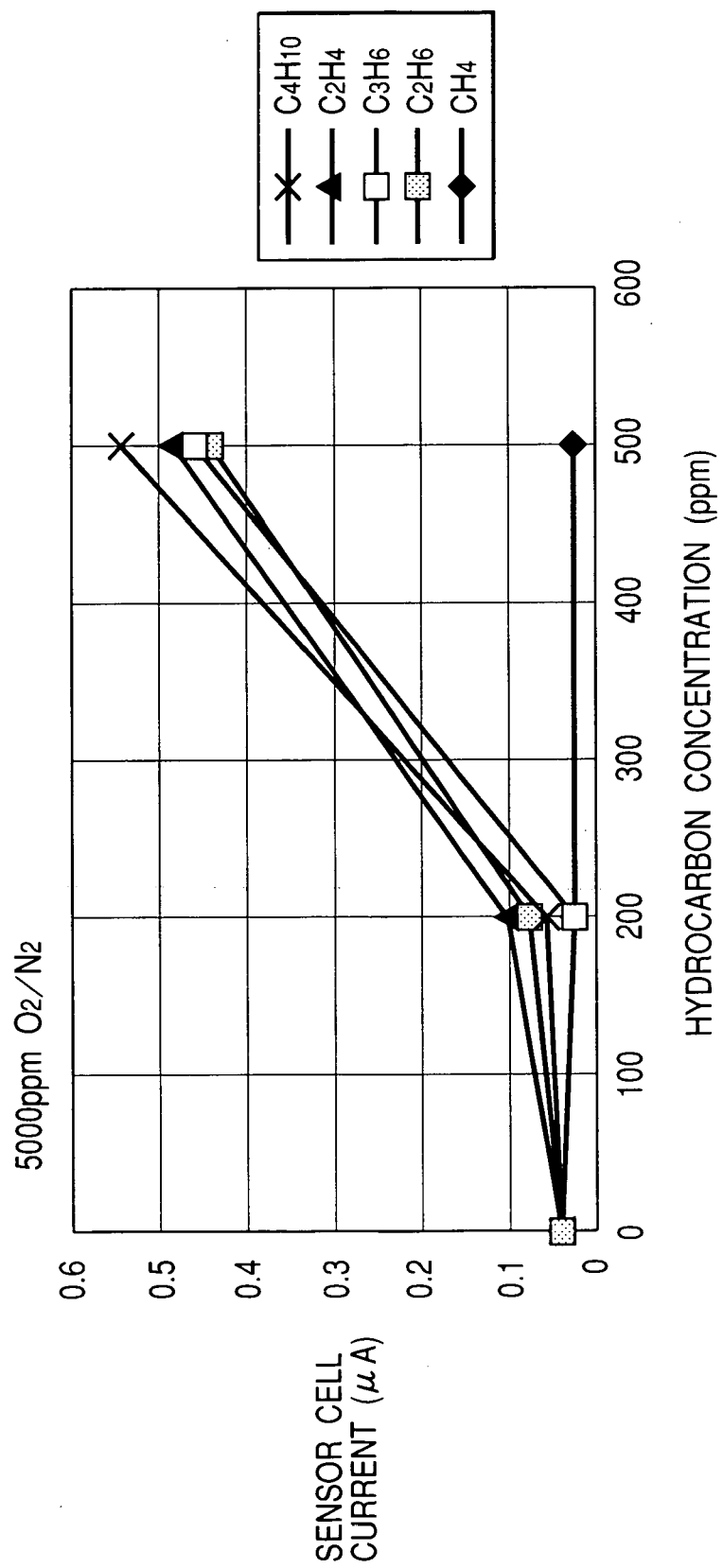
FIG. 12 is a diagram of the relation among a sensor cell current, a hydrocarbon concentration, and a hydrocarbon type which occurs in the gas sensor of FIG. 11.

FIG. 12 shows the relation among the measured sensor cell current, the methane ($CH_4$) concentration, the ethane ($C_2H_6$) concentration, the propylene ($C_3H_6$) concentration, the ethylene ($C_2H_4$) concentration, and the butane ($C_4H_{10}$) concentration which was obtained by the experiments on the gas sensor 1C. As understood from FIG. 11, the gas sensor 1C has high sensitivities with respect to hydrocarbons other than methane ($CH_4$).

Sixth Specific Embodiment

Figure 13:
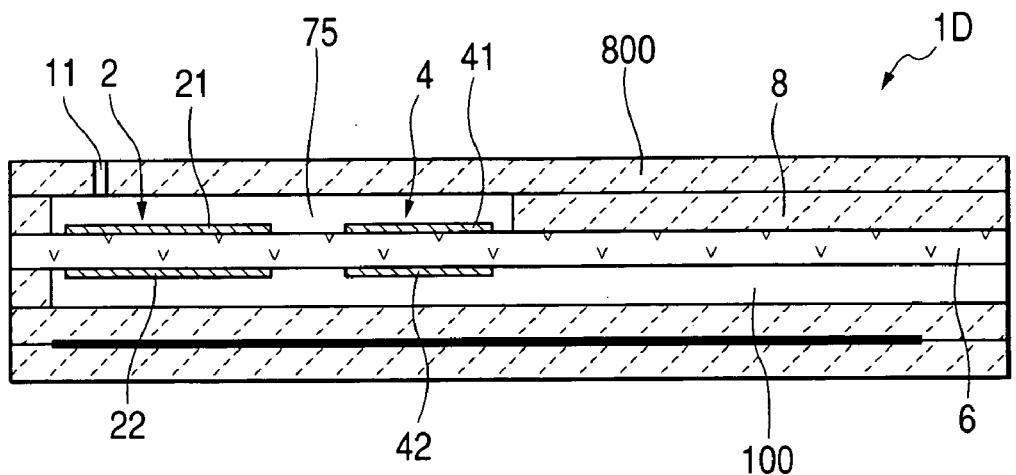
FIG. 13 is a sectional diagram of a gas sensor according to a sixth specific embodiment of this invention.

FIG. 13 shows a gas sensor 1D according to a sixth specific embodiment of this invention. The gas sensor 1D is similar to the gas sensors 1 (FIG. 2) except for design changes mentioned hereafter.

As shown in FIG. 13, the gas sensor 1D includes an oxygen pumping cell 2 and a sensor cell 4. The oxygen pumping cell 2 serves also as an oxygen monitor cell. A spacer 800 is superposed on the upper surface of the spacer 8. A measurement gas chamber 75 is defined among the spacer 800, the spacer 8, and the solid electrolyte member 6. The spacer 800 has a pinhole 11 via which a measurement gas is introduced into the measurement gas chamber 75.

The oxygen pumping cell 2 has the solid electrolyte member 6 and the electrodes 21 and 22. The solid electrolyte member 6 is sandwiched between the electrodes 21 and 22. The electrode 21 is exposed in the measurement gas chamber 75. The electrode 22 is exposed in the reference gas chamber 100.

The sensor cell 4 has the solid electrolyte member 6 and the electrodes 41 and 42. The solid electrolyte member 6 is sandwiched between the electrodes 41 and 42. The electrode 41 is exposed in the measurement gas chamber 75. The electrode 42 is exposed in the reference gas chamber 100.

Seventh Specific Embodiment

Figure 14:
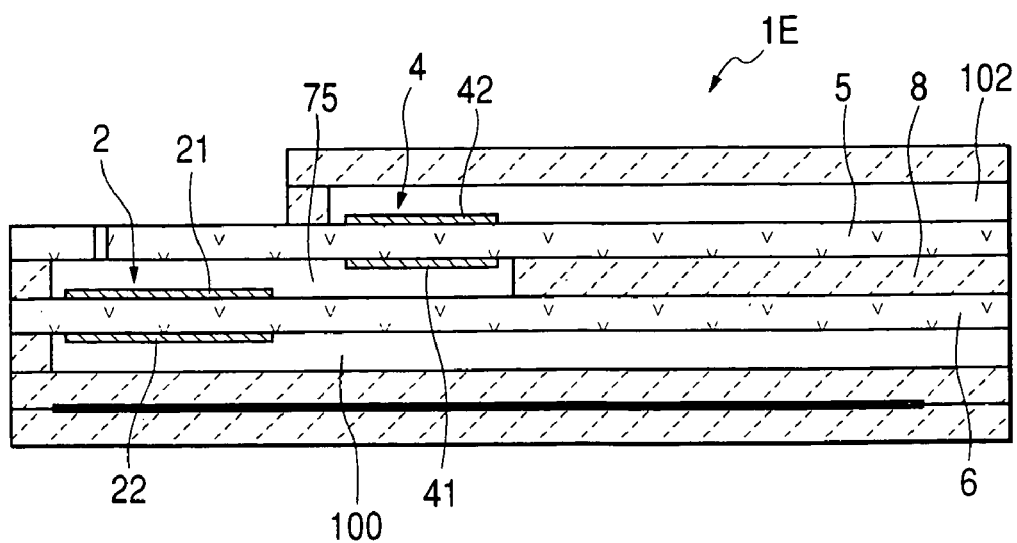
FIG. 14 is a sectional diagram of a gas sensor according to a seventh specific embodiment of this invention.

FIG. 14 shows a gas sensor 1E according to a seventh specific embodiment of this invention. The gas sensor 1E is similar to the gas sensors 1A (FIG. 9) except for design changes mentioned hereafter.

As shown in FIG. 14, the gas sensor 1E includes an oxygen pumping cell 2 and a sensor cell 4. The oxygen pumping cell 2 serves also as an oxygen monitor cell. The gas sensor 1E has a measurement gas chamber 75 into which a measurement gas is introduced. The measurement gas chamber 75 is defined among the solid electrolyte member 5, the spacer 8, and the solid electrolyte member 6.

The oxygen pumping cell 2 has the solid electrolyte member 6 and the electrodes 21 and 22. The solid electrolyte member 6 is sandwiched between the electrodes 21 and 22. The electrode 21 is exposed in the measurement gas chamber 75. The electrode 22 is exposed in the reference gas chamber 100.

The sensor cell 4 has the solid electrolyte member 5 and the electrodes 41 and 42. The solid electrolyte member 5 is sandwiched between the electrodes 41 and 42. The electrode 41 is exposed in the measurement gas chamber 75. The electrode 42 is exposed in the reference gas chamber 102.

What is claimed is:

1. A gas sensor comprising:
a measurement gas chamber;
first means for introducing a measurement gas into the measurement gas chamber under a prescribed diffusion resistance;
an oxygen pumping cell for adjusting an oxygen concentration in the measurement gas chamber, the oxygen pumping cell having 1) a first solid electrolyte member, 2) a first pumping electrode, and 3) a second pumping electrode, the first solid electrolyte member having an oxygen-ion conductivity, the first pumping electrode being exposed in the measurement gas chamber and extending on a first surface of the first solid electrolyte member, the second pumping electrode extending on a second surface of the first solid electrolyte member and being separate from the measurement gas chamber;
second means for applying a voltage between the first and second pumping electrodes to activate the oxygen pumping cell;
an oxygen monitor cell having 1) a second solid electrolyte member, 2) a first monitor electrode, and 3) a second monitor electrode, the second solid electrolyte member having an oxygen-ion conductivity, the first monitor electrode being exposed in the measurement gas chamber and extending on a first surface of the second solid electrolyte member, the first monitor electrode having an oxidizing activity with respect to a specific component of the measurement gas, the second monitor electrode being exposed to a reference gas and extending on a second surface of the second solid electrolyte member;
a sensor cell having 1) a third solid electrolyte member, 2) a first sensor electrode, and 3) a second sensor electrode, the third solid electrolyte member having an oxygen-ion conductivity, the first sensor electrode being exposed in the measurement gas chamber and extending on a first surface of the third solid electrolyte member, the first sensor electrode having an oxidizing activity with respect to the specific component of the measurement gas which is lower than the oxidizing activity of the first monitor electrode, the second sensor electrode being exposed to the reference gas and extending on a second surface of the third solid electrolyte member;
third means for applying a voltage between the first and second monitor electrodes;
fourth means for detecting an oxygen-ion current in the oxygen monitor cell when the third means applies the voltage between the first and second monitor electrodes;
fifth means for applying a voltage between the first and second sensor electrodes;
sixth means for detecting an oxygen-ion current in the sensor cell when the fifth means applies the voltage between the first and second sensor electrodes; and
seventh means for detecting a concentration of the specific component of the measurement gas from a relation between the oxygen-ion currents detected by the fourth and sixth means,
wherein the seventh means comprises means for detecting the concentration of the specific component of the measurement gas from a difference between the oxygen-ion currents detected by the fourth and sixth means, and
wherein the specific component of the measurement gas comprises hydrocarbon.

2. A gas sensor as recited in claim 1, further comprising eighth means for controlling the voltage between the first and second pumping electrodes in response to the oxygen-ion current detected by the fourth means so that the oxygen-ion current detected by the fourth means will be maintained at a desired value.

3. A gas sensor as recited in claim 1, wherein the first pump electrode is higher than the first sensor electrode in oxidizing activity with respect to hydrocarbon.

4. A gas sensor as recited in claim 1, wherein the first pump electrode is higher than the first sensor electrode in oxidizing activity with respect to hydrocarbon different from methane.

5. A gas sensor as recited in claim 1, wherein the first monitor electrode oxidizes hydrocarbon.

6. A gas sensor as recited in claim 5, further comprising eighth means for controlling the oxygen pumping cell to maintain an oxygen concentration, which results from reaction between hydrocarbon and oxygen on the first monitor cell, at a constant value, wherein the first monitor electrode is higher than the first sensor electrode in oxidizing activity with respect to hydrocarbon.

7. A gas sensor as recited in claim 1, wherein the first sensor electrode is lower than the first monitor electrode in oxidizing activity with respect to hydrocarbon including methane.

8. A gas sensor as recited in claim 1, wherein the first sensor electrode is lower than the first monitor electrode in oxidizing activity with respect to hydrocarbon different from methane.

9. A gas sensor as recited in claim 3, wherein the first monitor electrode and the first sensor electrode are different in degree of oxygen adsorption so as to be different in oxidizing activity with respect to hydrocarbon.

10. A gas sensor as recited in claim 1, wherein each of the first monitor electrode and the first sensor electrode contains at least one of Pt, Pd, Rh, and Au as a main metal component, and also contains at least one of Ti, Ta, Nb, Al, W, Mo, Cr, Mn, Fe, Co, Ni, and Zr.

11. A gas sensor as recited in claim 10, wherein the first monitor electrode comprises an electrode material containing 99–80% Pt and 1–20% Au by weight, and the first sensor electrode comprises either an electrode material containing 99–80% Pt and 1–20% $TiO_2$ or an electrode material containing 99–80% Pd and 1–20% $TiO_2$.

12. A gas sensor as recited in claim 1, wherein oxygen ion sources for the oxygen-ion currents in the oxygen monitor cell and the sensor cell are oxygen molecules.

13. In a gas sensor comprising a measurement gas chamber, an oxygen pumping cell having a pumping electrode exposed in the measurement gas chamber, an oxygen monitor cell having a monitor electrode which is exposed in the measurement gas chamber and has an oxidizing activity with respect to a specific component of a measurement gas, and a sensor cell having a sensor electrode which is exposed in the measurement gas chamber and has an oxidizing activity with respect to the specific component of the measurement gas, wherein the oxidizing activity of the sensor electrode is lower than that of the monitor electrode, a method of detecting a gas concentration, comprising the steps of:

introducing the measurement gas into the measurement gas chamber under a prescribed diffusion resistance;

applying a voltage to the oxygen monitor cell;

applying a voltage to the sensor cell;

detecting an oxygen-ion current in the oxygen monitor cell;

detecting an oxygen concentration in the measurement gas chamber from the detected oxygen-ion current in the oxygen monitor cell;

applying a voltage to the oxygen pumping cell;

controlling the voltage applied to the oxygen pumping cell in response to the detected oxygen concentration in the measurement gas chamber to adjust the oxygen concentration in the measurement gas chamber;

detecting an oxygen-ion current in the sensor cell; and detecting a concentration of the specific component of the measurement gas from a relation between the detected oxygen-ion current in the oxygen monitor cell and the detected oxygen-ion current in the sensor cell, wherein the concentration-detecting step comprises a step of detecting the concentration of the specific component of the measurement gas from a difference between the detected oxygen-ion current in the oxygen monitor cell and the detected oxygen-ion current in the sensor cell, and wherein the specific component of the measurement gas comprises hydrocarbon.

14. A method as recited in claim 13, further comprises a step of controlling the voltage applied to the oxygen pumping cell in response to the detected oxygen-ion current in the oxygen monitor cell so that the detected oxygen-ion current in the oxygen monitor cell will be maintained at a desired value.

15. A gas sensor as recited in claim 13, wherein oxygen ion sources for the oxygen-ion currents in the oxygen monitor cell and the sensor cell are oxygen molecules.

16. A gas sensor comprising:

a measurement gas chamber;

first means for introducing a measurement gas into the measurement gas chamber under a prescribed diffusion resistance;

an oxygen pumping cell for adjusting an oxygen concentration in the measurement gas chamber, the oxygen pumping cell having 1) a first solid electrolyte member, 2) a first pumping electrode, and 3) a second pumping electrode, the first solid electrolyte member having an oxygen-ion conductivity, the first pumping electrode being exposed in the measurement gas chamber and extending on a first surface of the first solid electrolyte member, the first pumping electrode having an oxidizing activity with respect to a specific component of the measurement gas, the second pumping electrode extending on a second surface of the first solid electrolyte member and being separate from the measurement gas chamber;

second means for applying a voltage between the first and second pumping electrodes to activate the oxygen pumping cell;

a sensor cell having 1) a second solid electrolyte member, 2) a first sensor electrode, and 3) a second sensor electrode, the second solid electrolyte member having an oxygen-ion conductivity, the first sensor electrode being exposed in the measurement gas chamber and extending on a first surface of the second solid electrolyte member, the first sensor electrode having an oxidizing activity with respect to the specific component of the measurement gas which is lower than the oxidizing activity of the first pumping electrode, the second sensor electrode being exposed to a reference gas and extending on a second surface of the second solid electrolyte member;

third means for detecting an oxygen-ion current in the oxygen pumping cell when the second means applies the voltage between the first and second pumping electrodes;

fourth means for applying a voltage between the first and second sensor electrodes;

fifth means for detecting an oxygen-ion current in the sensor cell when the fourth means applies the voltage between the first and second sensor electrodes; and sixth means for detecting a concentration of the specific component of the measurement gas from a relation between the oxygen-ion currents detected by the third and fifth means, wherein the sixth means comprises means for detecting the concentration of the specific component of the measurement gas from a difference between the oxygen-ion currents detected by the third and fifth means, and wherein the specific component of the measurement gas comprises hydrocarbon.

17. A gas sensor as recited in claim 16, further comprising seventh means for controlling the oxygen concentration in the measurement gas chamber at a constant value in response to a relation between the voltage applied between the first and second pumping electrodes and the oxygen-ion current detected by the third means.

18. A gas sensor as recited in claim 16, wherein the first pumping electrode is higher than the first sensor electrode in oxidizing activity with respect to hydrocarbon.

19. A gas sensor as recited in claim 16, wherein the first pumping electrode is higher than the first sensor electrode in oxidizing activity with respect to hydrocarbon different from methane.

20. A gas sensor as recited in claim 16, wherein oxygen ion sources for the oxygen-ion currents in the oxygen monitor cell and the sensor cell are oxygen molecules.

21. In a gas sensor comprising a measurement gas chamber, an oxygen pumping cell having a pumping electrode which is exposed in the measurement gas chamber and has an oxidizing activity with respect to a specific component of a measurement gas, and a sensor cell having a sensor electrode which is exposed in the measurement gas chamber and has an oxidizing activity with respect to the specific component of the measurement gas, wherein the oxidizing activity of the sensor electrode is lower than that of the pumping electrode, a method of detecting a gas concentration, comprising the steps of:

introducing the measurement gas into the measurement gas chamber under a prescribed diffusion resistance;
    applying a voltage to the oxygen pumping cell;
    applying a voltage to the sensor cell;
    detecting an oxygen-ion current in the oxygen pumping cell;
    detecting an oxygen-ion current in the sensor cell; and
    detecting a concentration of the specific component of the measurement gas from a relation between the detected oxygen-ion current in the oxygen pumping cell and the detected oxygen-ion current in the sensor cell,
    wherein the concentration-detecting step comprises the step of detecting the concentration of the specific component of the measurement gas from a difference between the detected oxygen-ion current in the oxygen pumping cell and the detected oxygen-ion current in the sensor cell, and
    wherein the specific component of the measurement gas comprises hydrocarbon.

22. A method as recited in claim 21, further comprising the step of controlling an oxygen concentration in the measurement gas chamber at a constant value in response to a relation between the voltage applied to the oxygen pumping cell and the detected oxygen-ion current in the oxygen pumping cell.

23. A gas sensor as recited in claim 21, wherein oxygen ion sources for the oxygen-ion currents in the oxygen monitor cell and the sensor cell are oxygen molecules.

* * * * *